United States Patent
Sillacci Melkko et al.

(10) Patent No.: US 9,315,557 B2
(45) Date of Patent: Apr. 19, 2016

(54) IL-17A BINDING MOLECULES AND MEDICAL USES THEREOF

(71) Applicant: COVAGEN AG, Schlieren (CH)

(72) Inventors: Michela Sillacci Melkko, Schlieren (CH); Nadja Banziger, Schlieren (CH); Richard Woods, Schlieren (CH); Wenjuan Zha, Schlieren (CH); Isabella Attinger, Schlieren (CH); Roger Santimaria, Schlieren (CH); Wibke Lembke, Schlieren (CH); Sarah Batey, Schlieren (CH); Ulrike Von Der Bey, Schlieren (CH); Julian Bertschinger, Schlieren (CH); Dragan Grabulovski, Schlieren (CH)

(73) Assignee: Covagen AG, Schlieren (CH)

( * ) Notice: Subject to any disclaimer, the term of this patent is extended or adjusted under 35 U.S.C. 154(b) by 0 days.

(21) Appl. No.: 14/428,245

(22) PCT Filed: Sep. 19, 2013

(86) PCT No.: PCT/EP2013/069481
§ 371 (c)(1),
(2) Date: Mar. 13, 2015

(87) PCT Pub. No.: WO2014/044758
PCT Pub. Date: Mar. 27, 2014

(65) Prior Publication Data
US 2015/0322125 A1 Nov. 12, 2015

(30) Foreign Application Priority Data
Sep. 21, 2012 (EP) .................... 12185425

(51) Int. Cl.
C07K 14/435 (2006.01)
C07K 14/47 (2006.01)
C07K 16/24 (2006.01)
A61K 38/17 (2006.01)
A61K 38/16 (2006.01)

(52) U.S. Cl.
CPC ............ *C07K 14/4703* (2013.01); *A61K 38/16* (2013.01); *A61K 38/1709* (2013.01); *C07K 16/241* (2013.01); *C07K 16/244* (2013.01); *C07K 2317/92* (2013.01); *C07K 2317/94* (2013.01); *C07K 2318/20* (2013.01); *C07K 2319/00* (2013.01); *C07K 2319/30* (2013.01)

(58) Field of Classification Search
None
See application file for complete search history.

(56) References Cited

FOREIGN PATENT DOCUMENTS

WO  WO 2011/023685  3/2011
WO  WO 2012/159836  11/2012

OTHER PUBLICATIONS

Miossec & Kolls "Targeting IL 17 and TH17 cells in chronic inflammation" Nature Reviews, Drug Discovery, vol. 11, Oct. 2012, 763-776.*
Covagen Advance Biopharmaceuticals, *Covagen utilizes the unique versatility of Fynomers to create next generation biologics*, Internet Citation, Nov. 1, 2011; p. 1.
E. Dhimolea, et al., World Bispecific Antibody Summit; *Mabs Landes Bioscience*, US., Sep. 27-28, 2011; pp. 4-16, vol. 4, No. 1, Boston, MA.
M. Koenders, et al.; *Tumor Necrosis Factor—Interleukin-17 Interplay Induces S100A8*; Arthritis & Rheumatism, John Wiley & Sons, Inc., US, vol. 63, No. 8, Aug. 1, 2011; pp. 2329-2339 (Abstract).
International Search Report and Written Opinion of the International Searching Authority; Dec. 5, 2013.
Ekerjung, et al. *mAbs*4(1): 14 Poster session: Sep. 27-28, 2011, "Bispecific Affibody Molecules for Targeting of EGFR and HER2."
Hurst, et al. *The Journal Immunology*169: 443-453 2002 "New IL-17 Family Members Promote Th1 or Th2 Responses in the Lung: In Vivo Function of the Novel Cytokine IL-25."

* cited by examiner

*Primary Examiner* — Christina Bradley
(74) *Attorney, Agent, or Firm* — Hunton & Williams LLP

(57) ABSTRACT

The present invention relates to a polypeptide inhibiting the activity of glycosylated IL-17A, wherein the polypeptide comprises or consists of an amino acid sequence selected from the group consisting of: (a) GVTLFVALYDY($X^1$)($X^2$)($X^3$)($X^4$)($X^5$)($X^6$) DLSFHKGEKFQIL STHEYEDWWEARSLTTGETGYIPSNYVAPVDSIQ (SEQ ID NO: 1), wherein amino acid positions ($X^1$) to ($X^6$) may be any amino acid sequence; and (b) an amino acid sequence which is at least 85% identical to the amino acid sequence of (a), wherein the identity determination excludes amino acid positions ($X^1$) to ($X^6$) and provided that the amino acid sequence STHEYE (SEQ ID NO: 2) in amino acid positions 31 to 36 of SEQ ID NO: 1 is conserved. The invention also relates to fusion constructs, compositions and medical uses comprising said polypeptide.

18 Claims, 18 Drawing Sheets

Figure 1
A
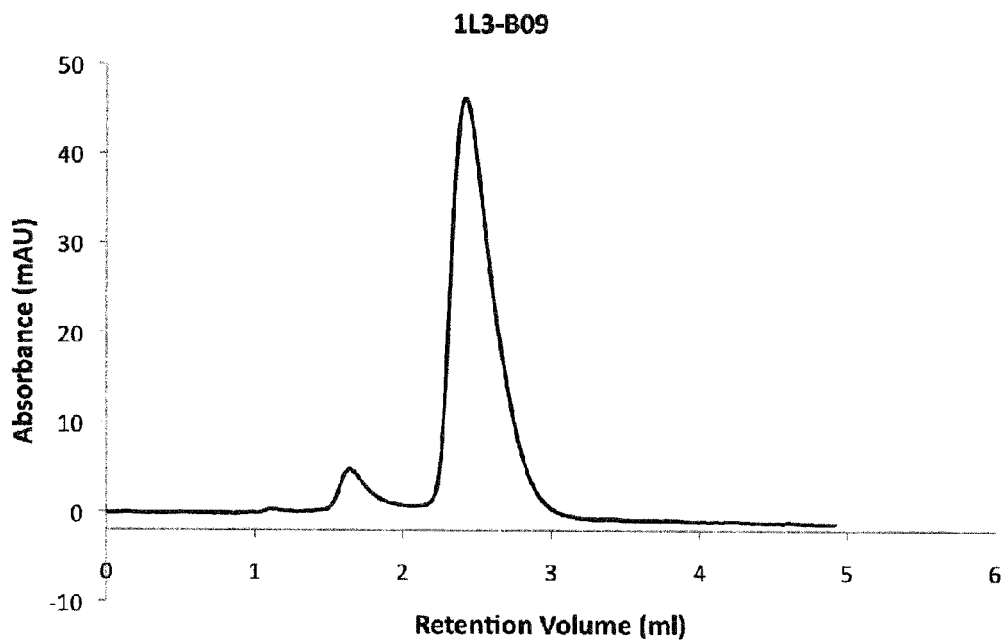
B
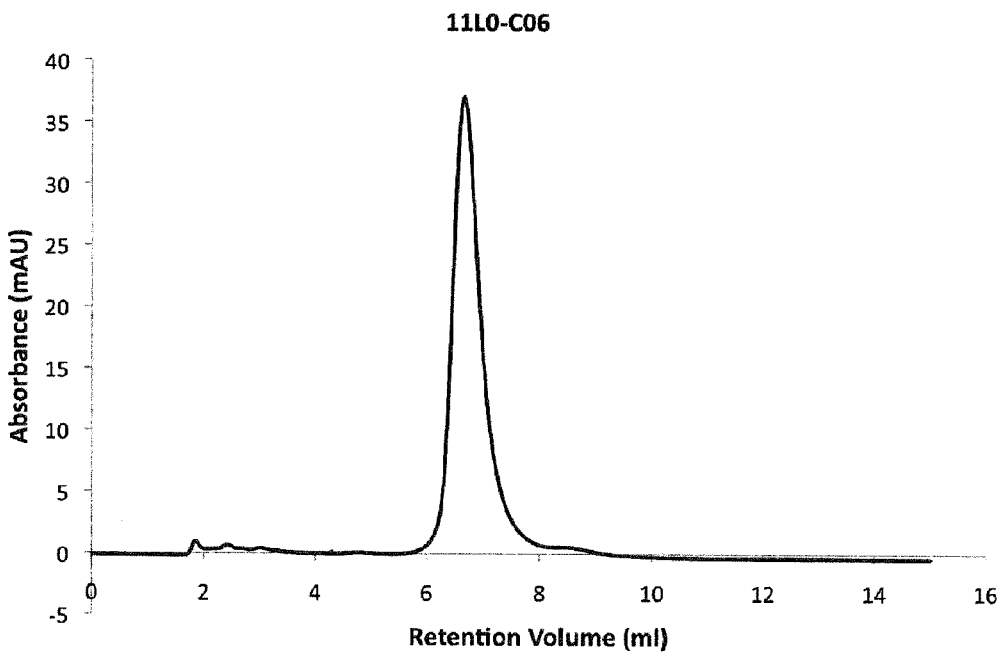

Figure 1 - continued
C
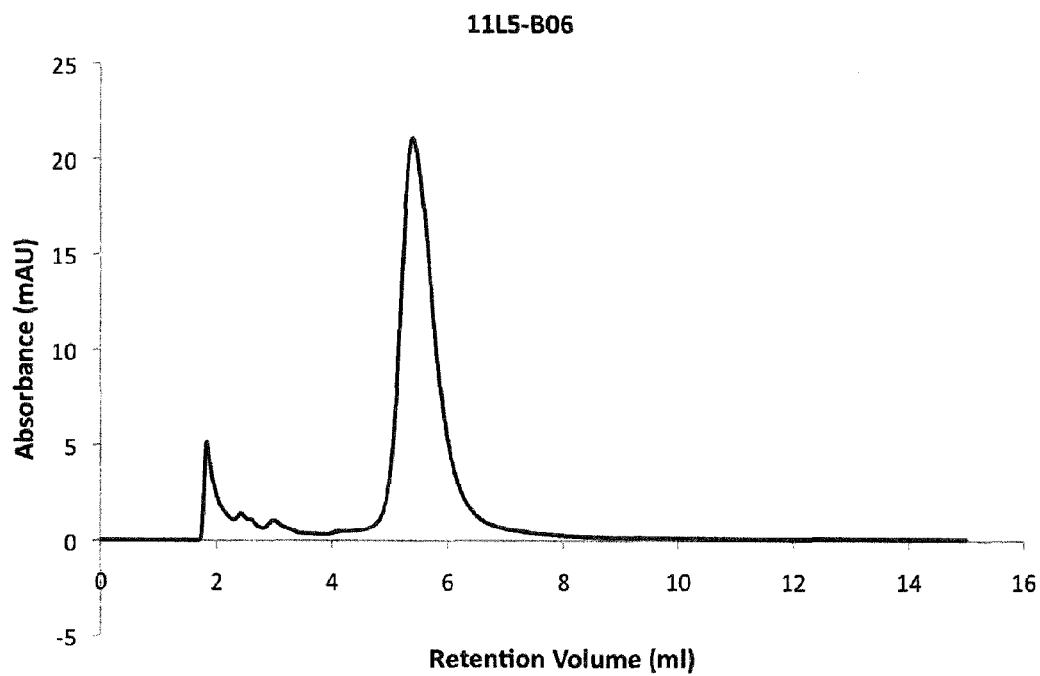
D
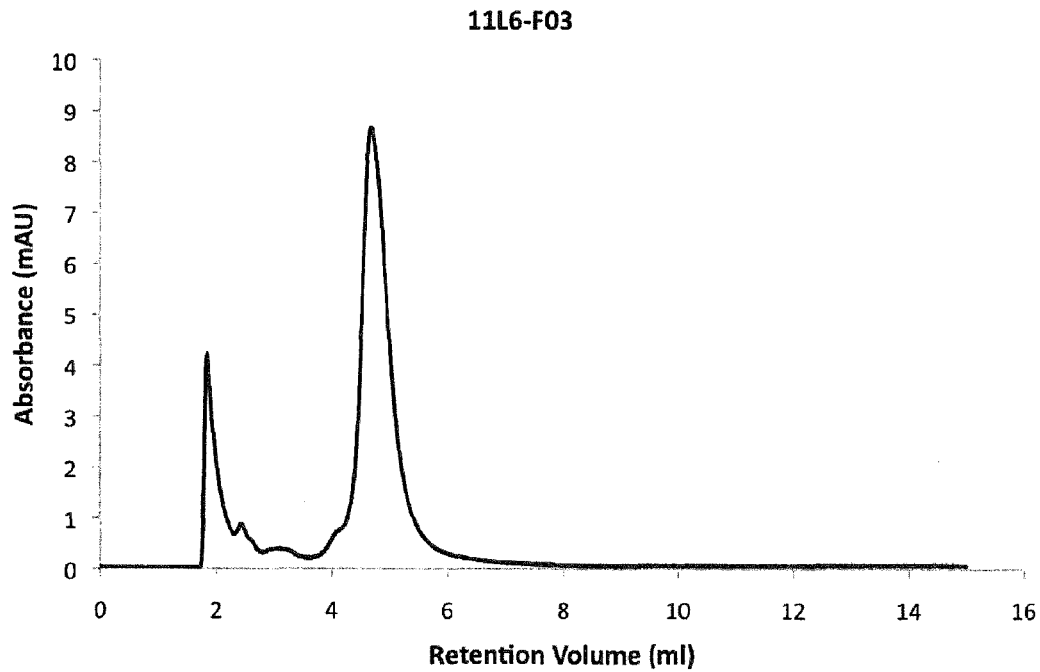

Figure 1 - continued
E
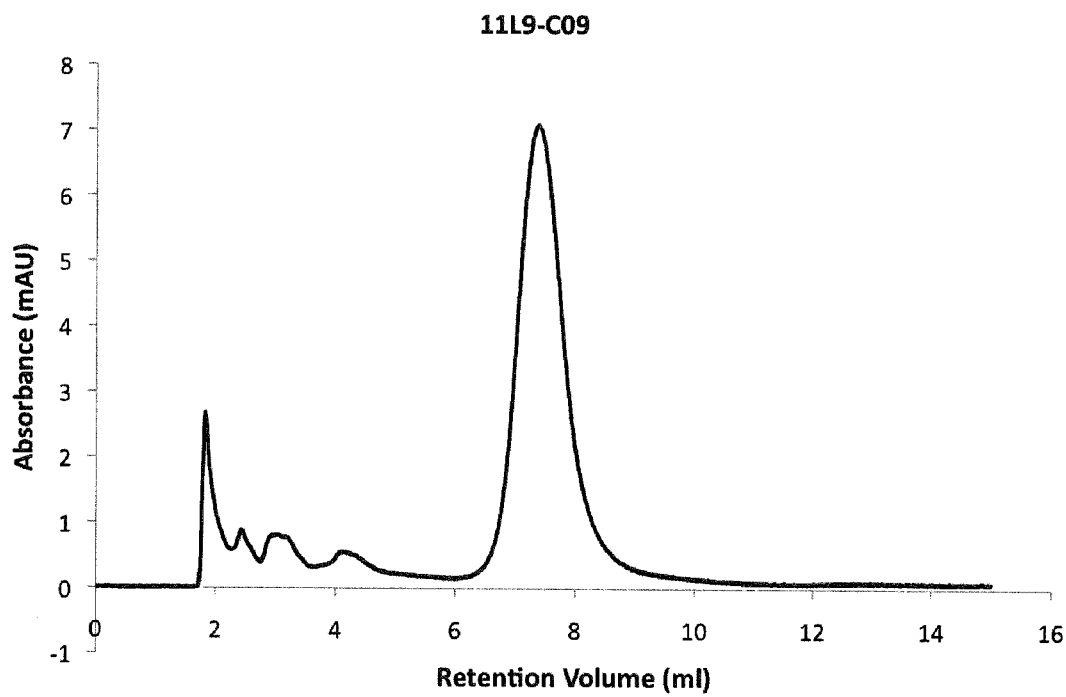
F
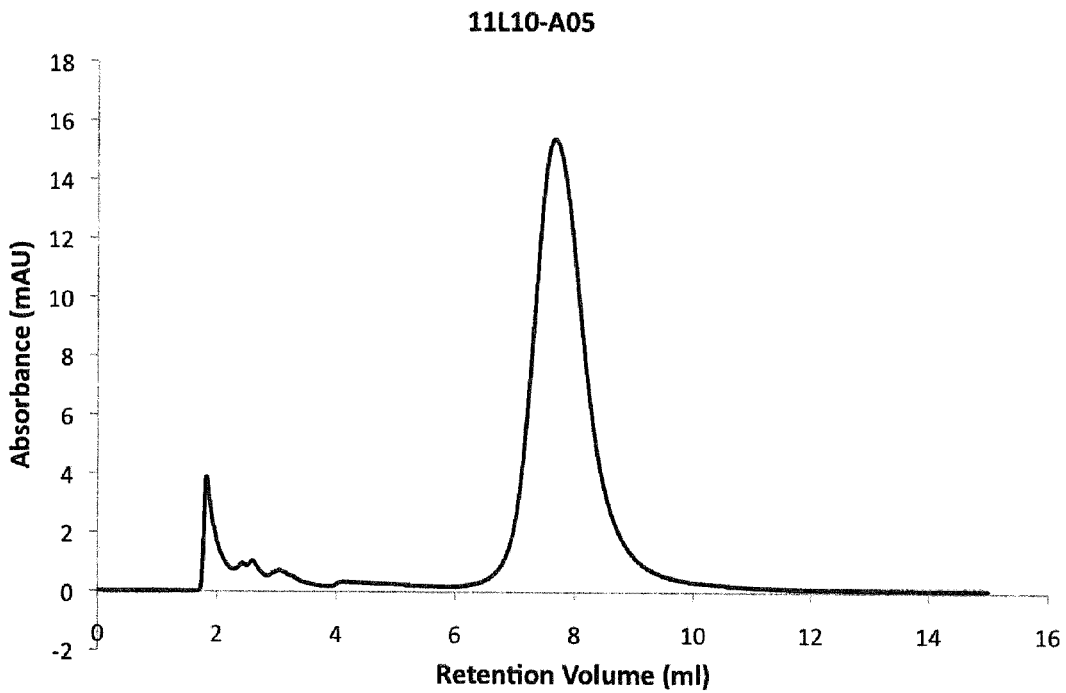

Figure 1 - continued
G
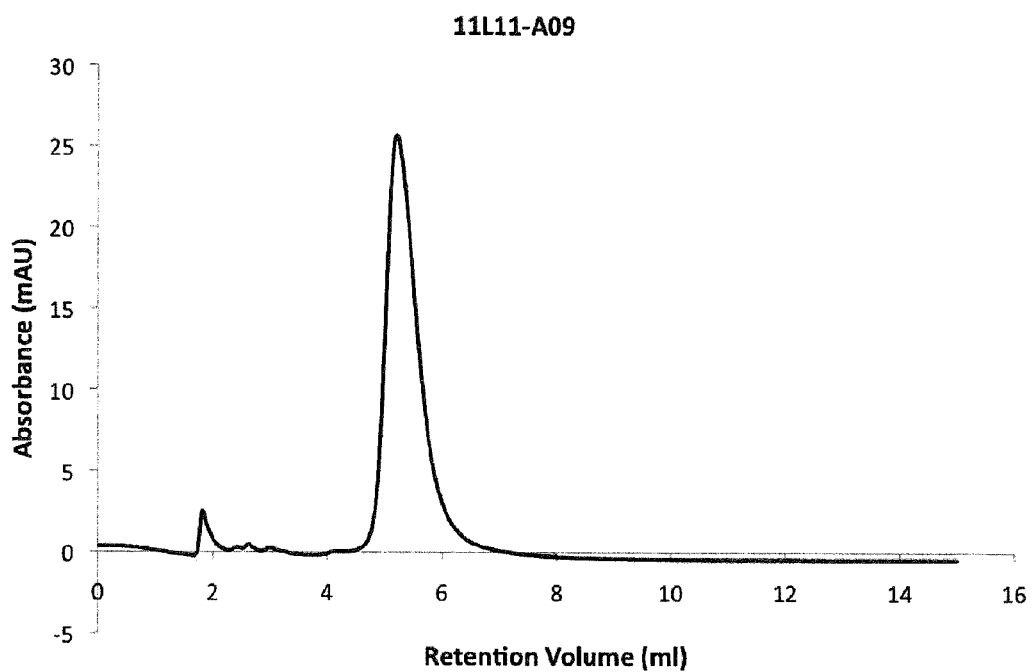

Figure 2 – continued
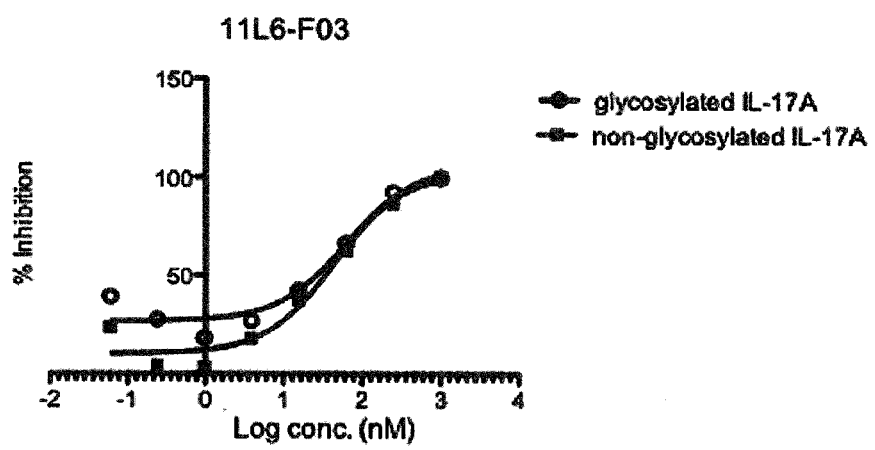
D 11L6-F03
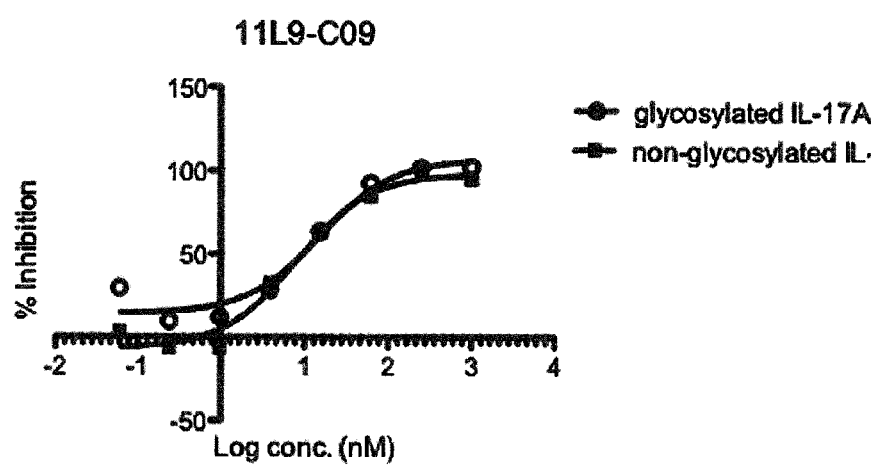
E 11L9-C09
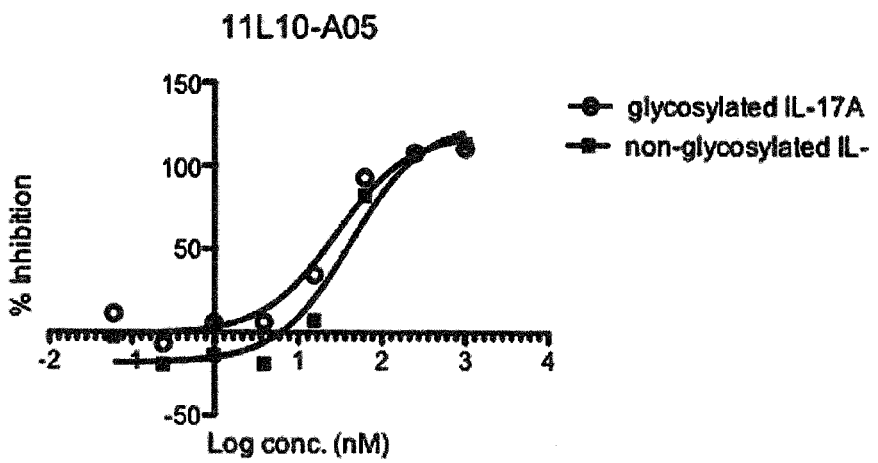
F 11L10-A05

Figure 3
A
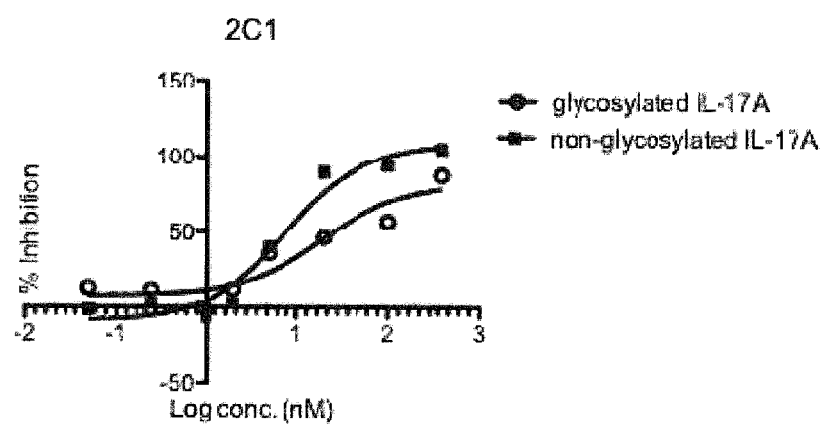
B
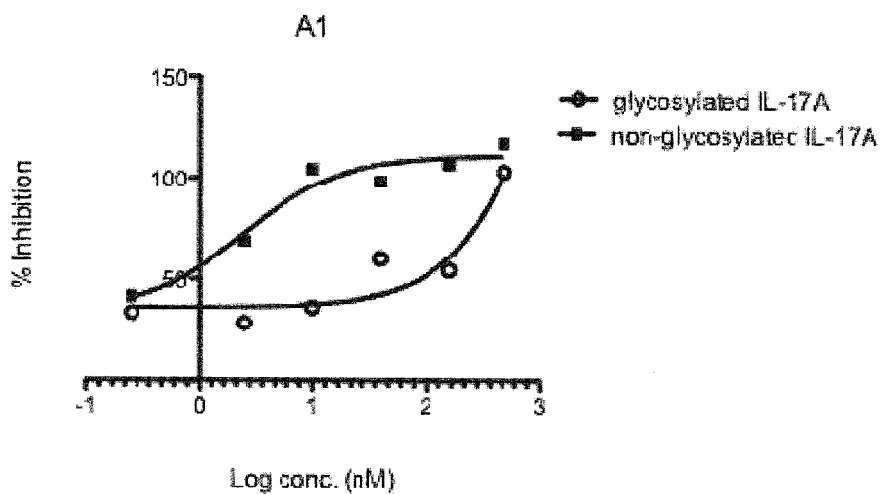
C
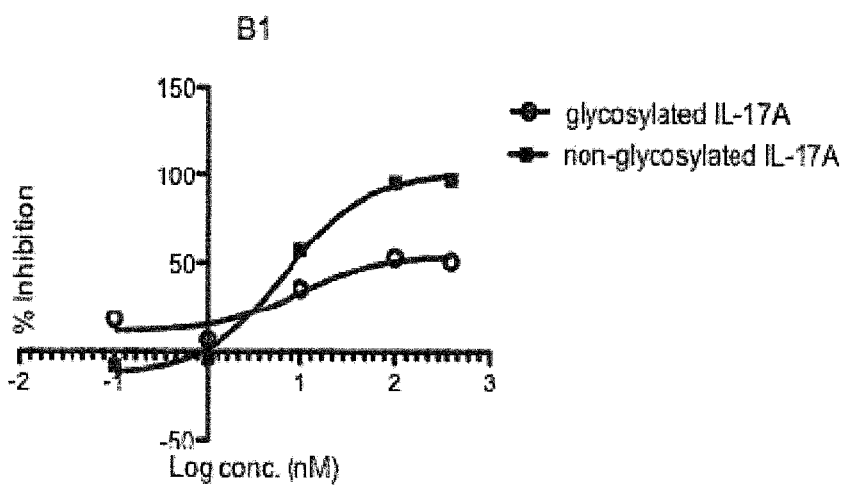

Figure 5
A
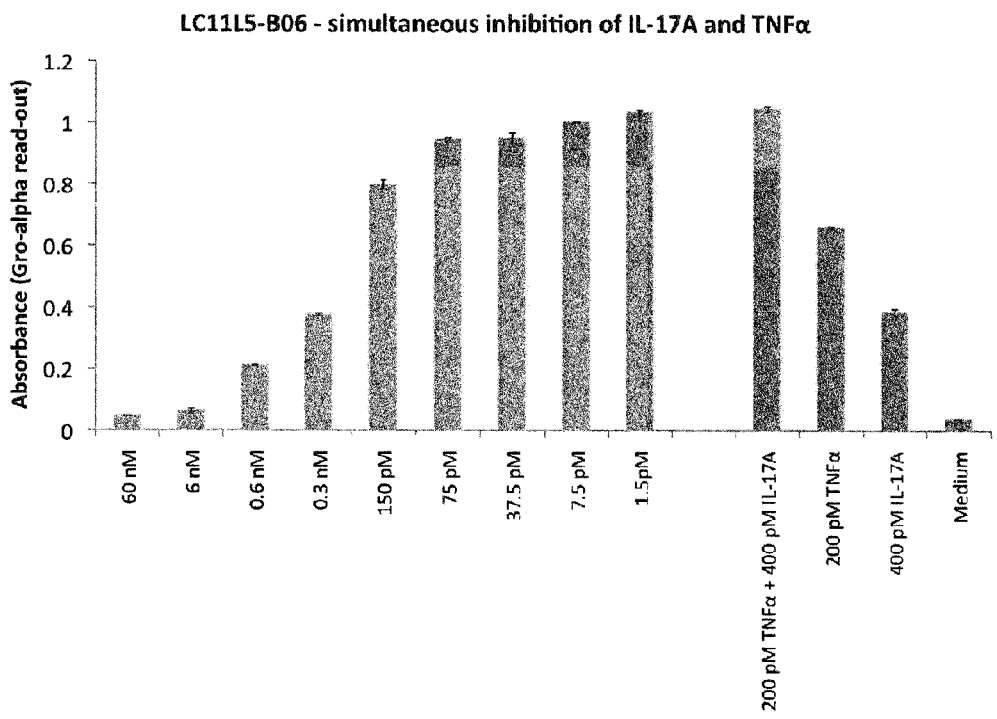
B
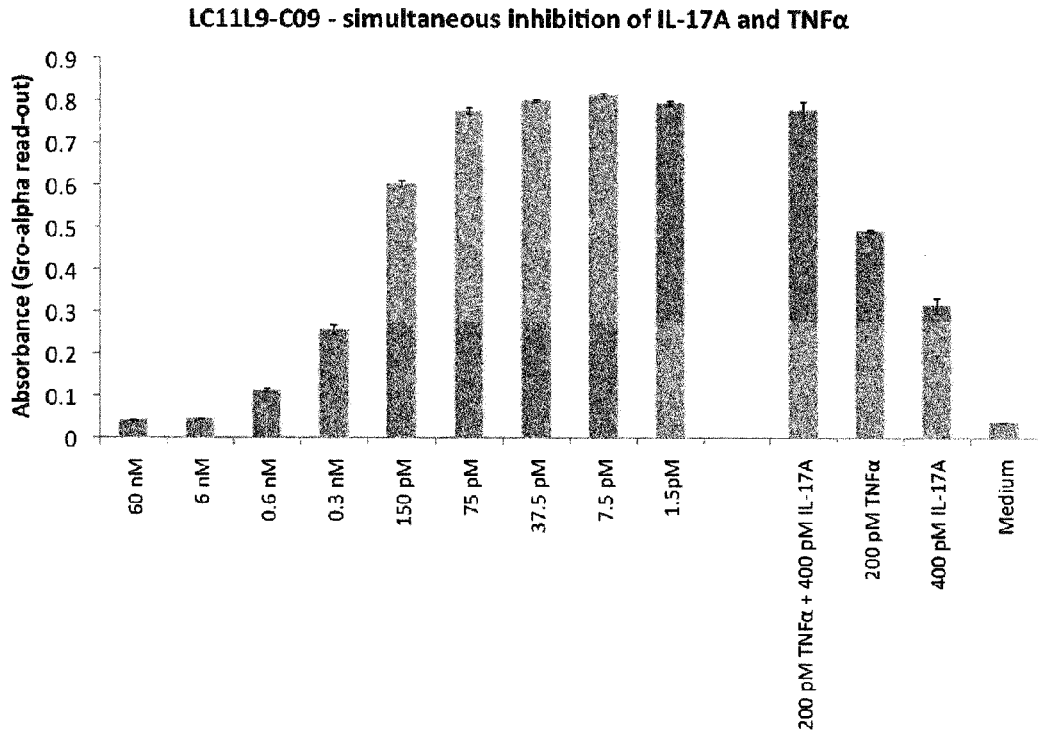

A

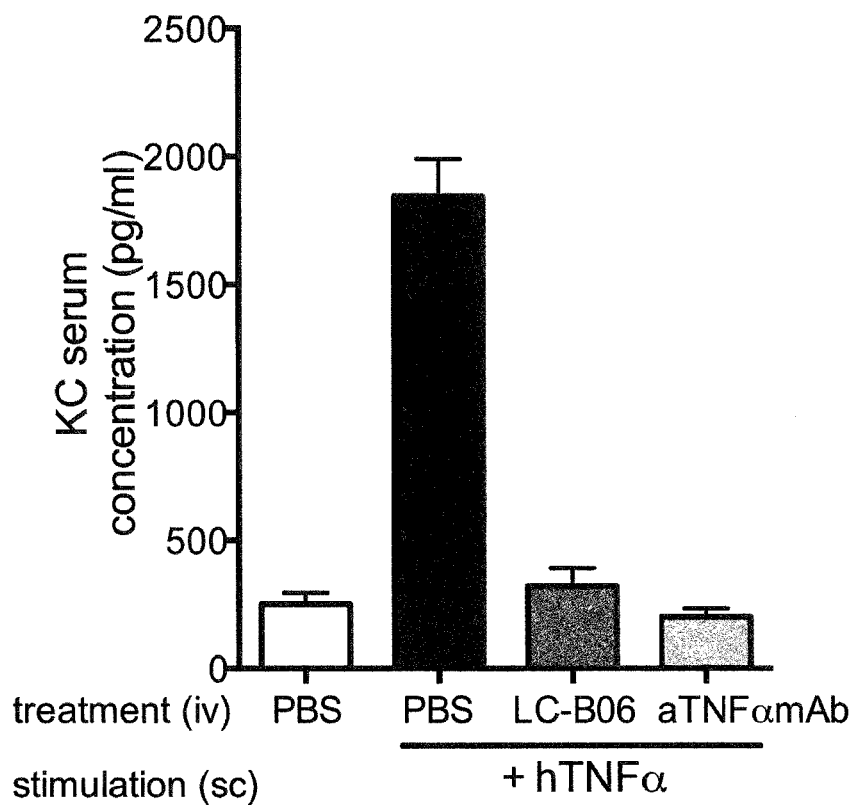
Figure 6 - continued
B

Figure 6 – continued
C
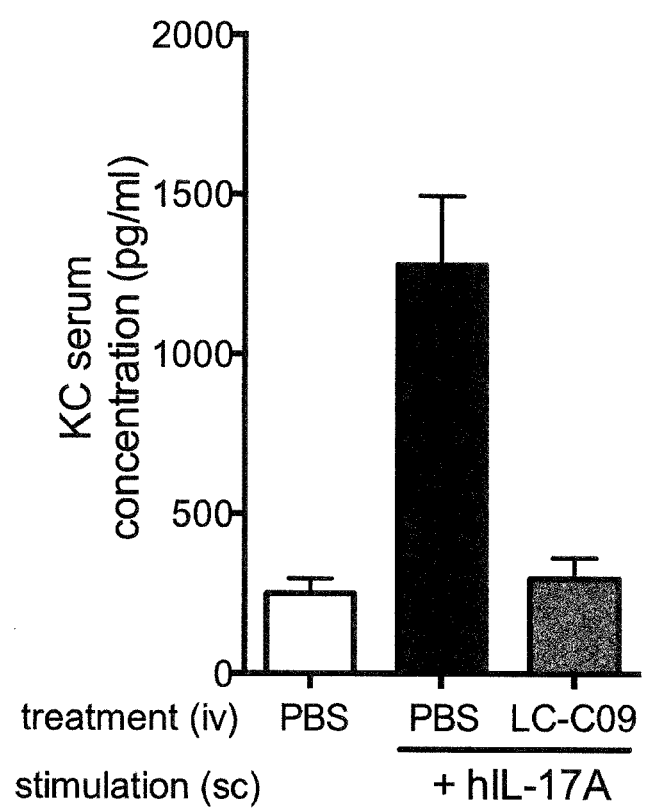

Figure 6 - continued
D
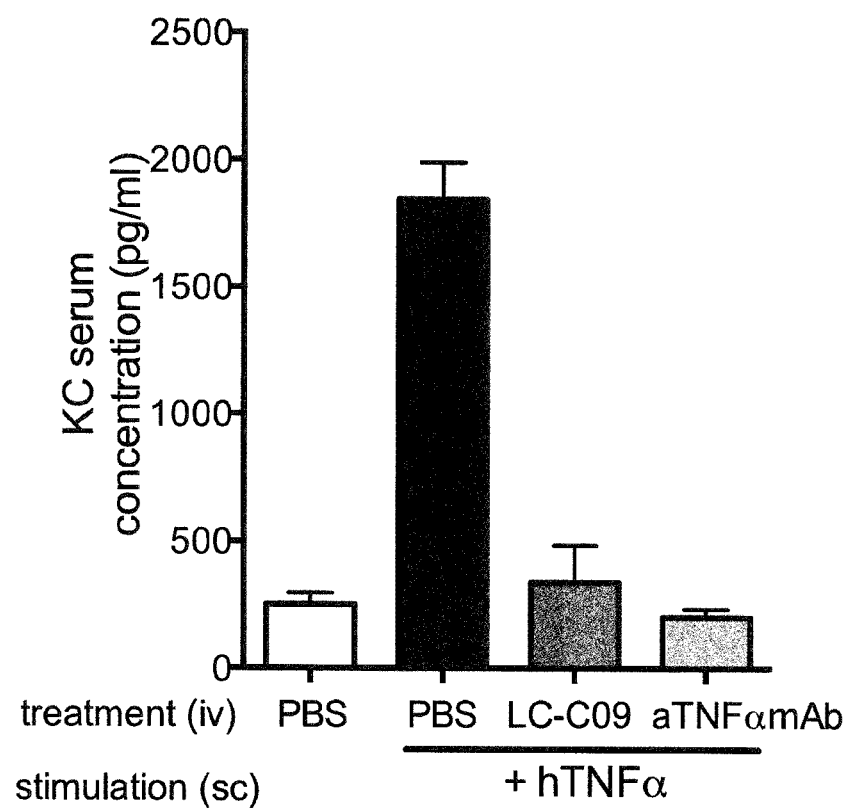

Figure 7
A
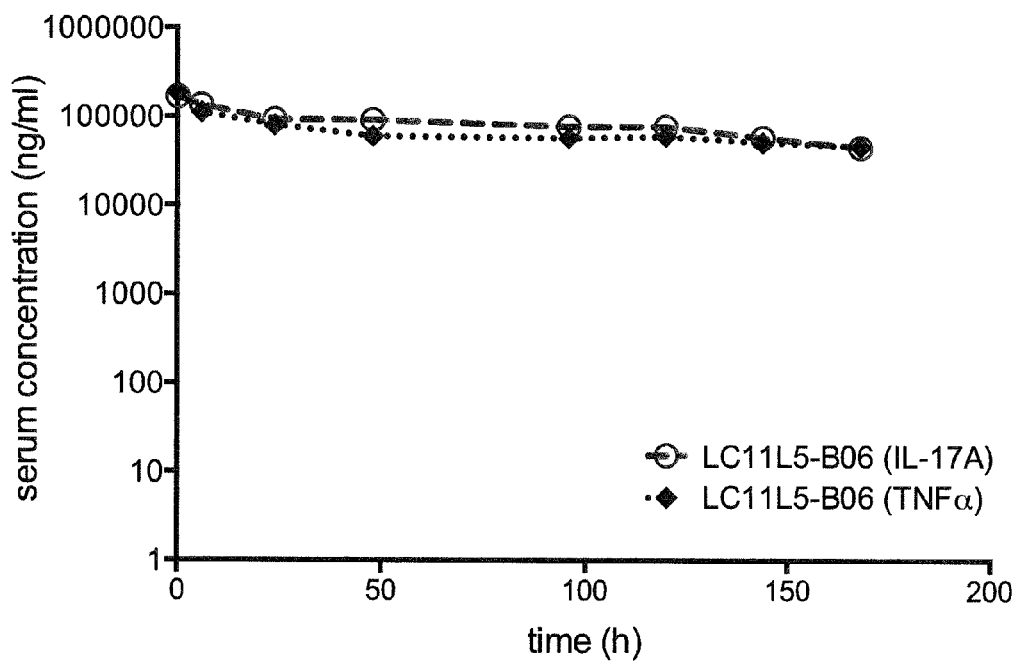
B
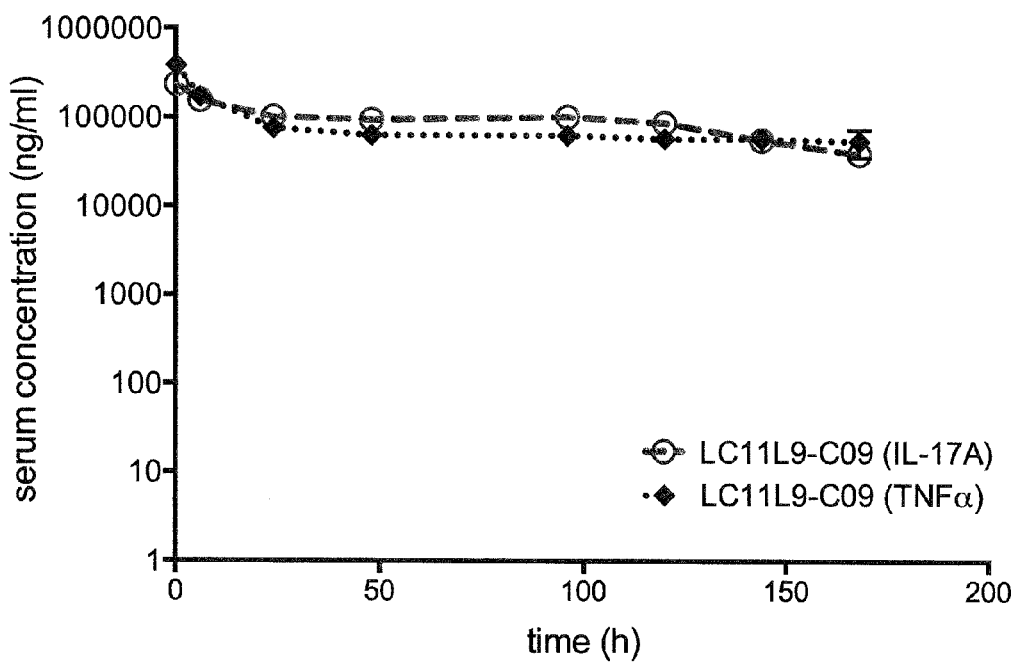

Figure 8

```
                              10        20        30        40
FynSH3wt  (SEQ ID NO: 20) GVTLFVALYDYEARTEDDLSFHKGEKFQILNSSE-GDWWE
1L3-B9    (SEQ ID NO:  3) GVTLFVALYDYANHGNRDLSFHKGEKFQILSTHEYEDWWE
11L0-C6   (SEQ ID NO:  4) GVTLFVALYDYKQKGHLDLSFHKGEKFQILSTHEYEDWWE
11L5-B06  (SEQ ID NO:  5) GVTLFVALYDYSARGQLDLSFHKGEKFQILSTHEYEDWWE
11L6-F03  (SEQ ID NO:  6) GVTLFVALYDYDKLSALDLSFHKGEKFQILSTHEYEDWWE
11L9-C09  (SEQ ID NO:  7) GVTLFVALYDYESVSWSDLSFHKGEKFQILSTHEYEDWWE
11L10-A05 (SEQ ID NO:  8) GVTLFVALYDYSSRGVLDLSFHKGEKFQILSTHEYEDWWE
11L11-A09 (SEQ ID NO:  9) GVTLFVALYDYSRKSNLDLSFHKGEKFQILSTHEYEDWWE
                          **********    ************    *   ****

50        60
FynSH3wt  (SEQ ID NO: 20) ARSLTTGETG YIPSNYVAPVDSIQ
1L3-B9    (SEQ ID NO:  3) ARSLTTGETG YIPSNYVAPVDSIQ
11L0-C6   (SEQ ID NO:  4) ARSLTTGETG YIPSNYVAPVDSIQ
11L5-B06  (SEQ ID NO:  5) ARSLTTGETG YIPSNYVAPVDSIQ
11L6-F03  (SEQ ID NO:  6) ARSLTTGETG YIPSNYVAPVDSIQ
11L9-C09  (SEQ ID NO:  7) ARSLTTGETG YIPSNYVAPVDSIQ
11L10-A05 (SEQ ID NO:  8) ARSLTTGETG YIPSNYVAPVDSIQ
11L11-A09 (SEQ ID NO:  9) ARSLTTGETG YIPSNYVAPVDSIQ
                          ************************
```

Figure 9

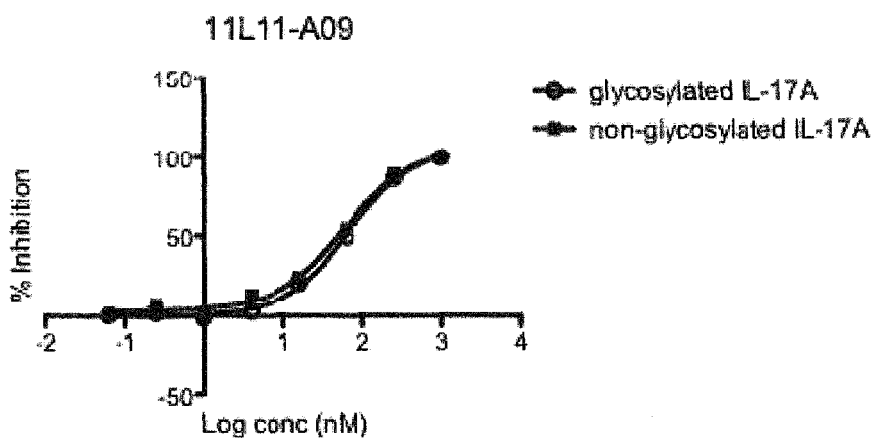

Figure 12
A
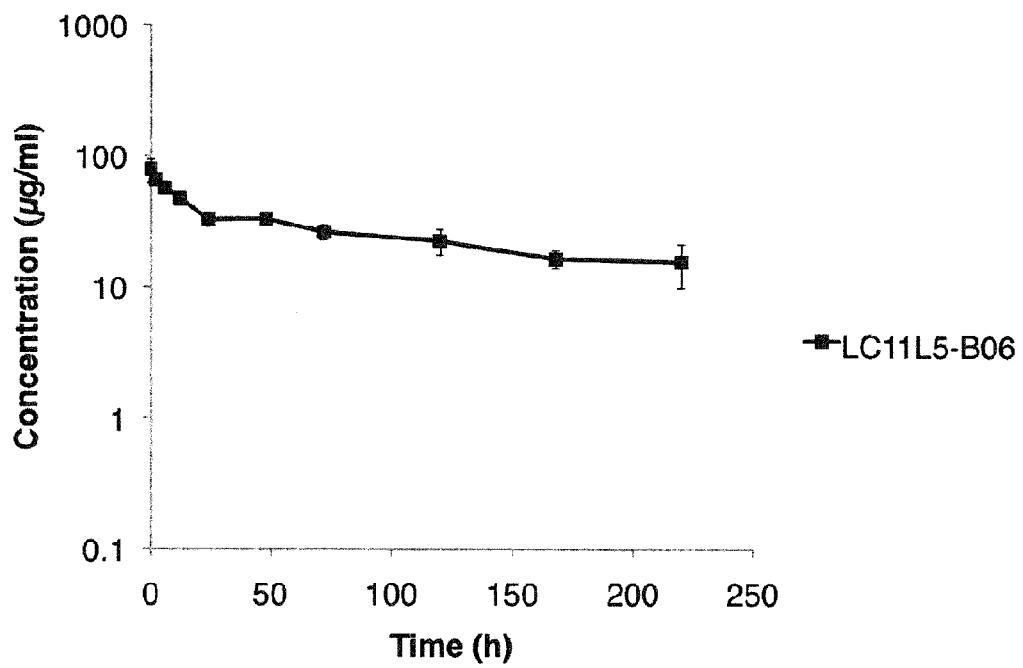
B
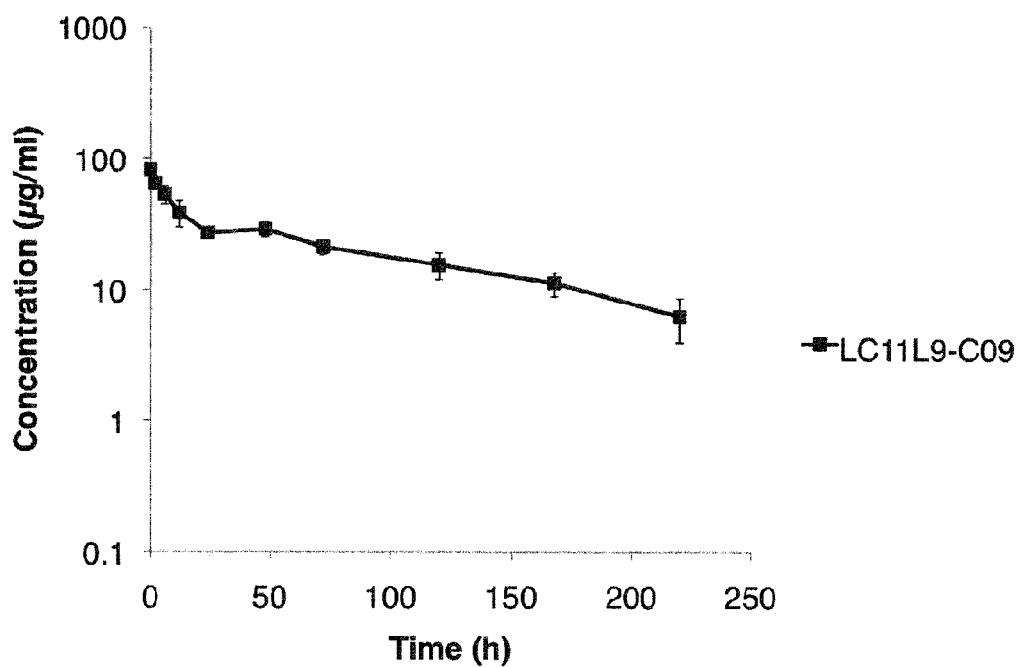

Figure 13
A
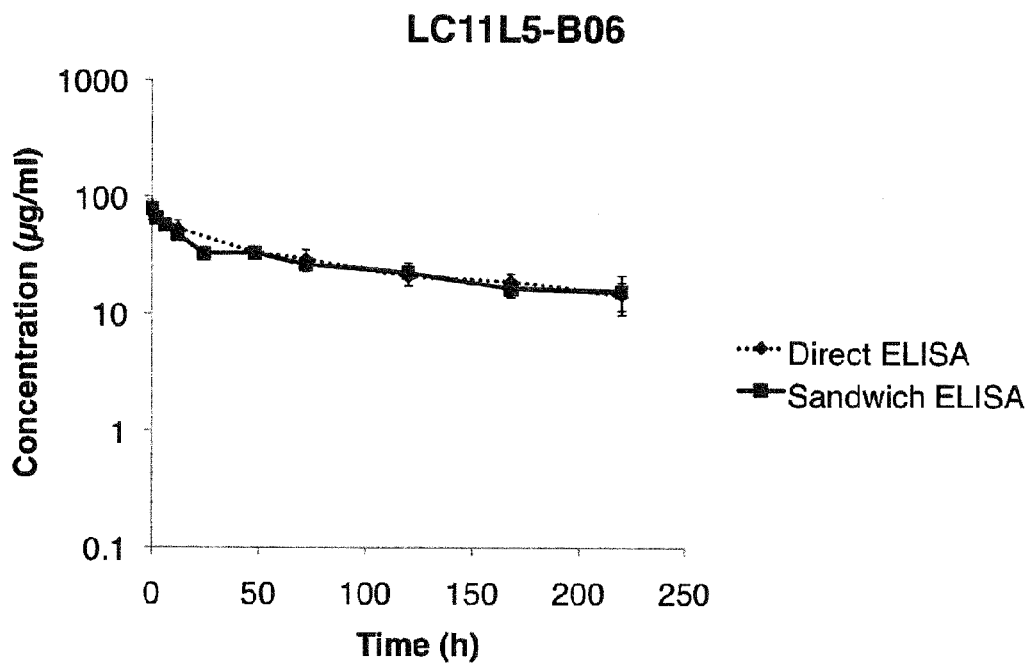
B
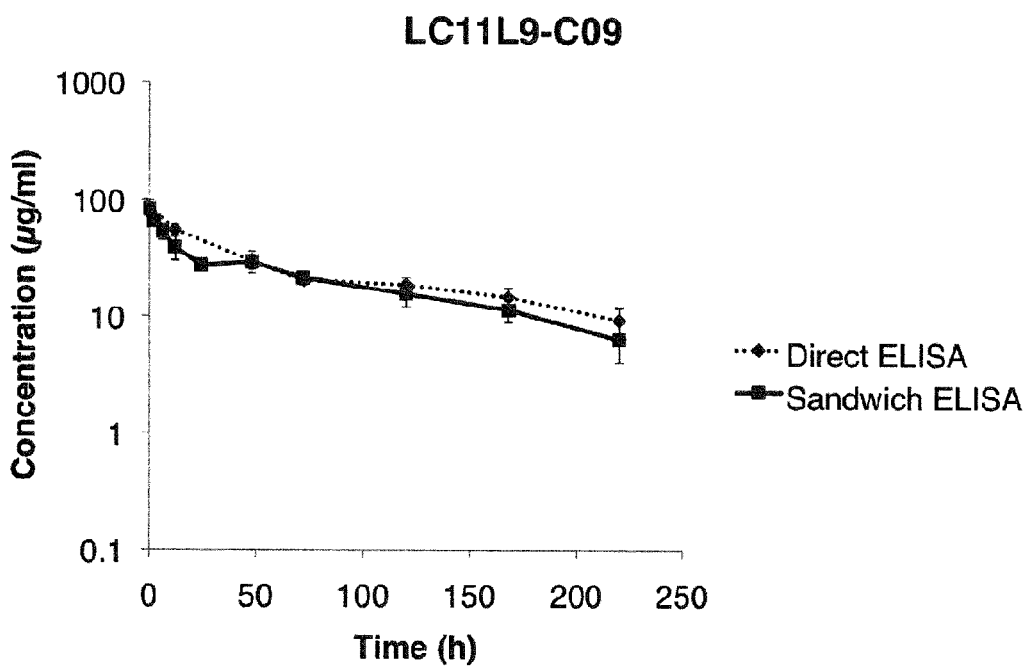

IL-17A BINDING MOLECULES AND MEDICAL USES THEREOF

CROSS-REFERENCE TO RELATED APPLICATIONS

This application is the U.S. National Stage filing of International Application No. PCT/EP2013/069481, filed Sep. 19, 2013, which claims priority to EP 12185425.1, filed Sep. 21, 2012, the disclosure of each of which are hereby incorporated by reference.

The present invention relates to a polypeptide inhibiting the activity of glycosylated IL-17A, wherein the polypeptide comprises or consists of an amino acid sequence selected from the group consisting of: (a) GVTLFVALYDY($X^1$)($X^2$)($X^3$)($X^4$)($X^5$)($X^6$)DLSFHKGEKFQIL STHEYEDWWEARSLTTGETGYIPSNYVAPVDSIQ (SEQ ID NO: 1), wherein amino acid positions ($X^1$) to ($X^6$) may be any amino acid sequence; and (b) an amino acid sequence which is at least 85% identical to the amino acid sequence of (a), wherein the identity determination excludes amino acid positions ($X^1$) to ($X^6$) and provided that the amino acid sequence STHEYE (SEQ ID NO: 2) in amino acid positions 31 to 36 of SEQ ID NO: 1 is conserved. The invention also relates to fusion constructs, compositions and medical uses comprising said polypeptide.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

CD4+ T cells play a central role in orchestrating immune responses by assisting other cells of the adaptive or innate immune system. In early studies two classes of CD4+ T cells (Th1 and Th2) were identified. More recently, a new subset of CD4+ T cells, the Th17 lineage was identified. Th17 cells appear to have evolved as a branch of the adaptive immune system specialized in enhanced host protection against extracellular bacteria as well as some fungi and microbes not well covered by Th1 or Th2 immunity.

Th17 cells were identified in the context of the discovery of a new cytokine family, the IL-17 family, which is presently known to comprise six members (IL-17A-F). IL-17 (previously named CTLA-8) is mainly expressed by Th17 cells and was designated IL-17A to indicate that it is the founding member of this cytokine family. Human interleukin-17A (IL-17) is a pleiotropic, pro-inflammatory cytokine that is key to the definition of the CD4+T helper 17 (TH17) cell lineage, as mentioned above (Miossec P. et al. (2009) N. Engl. J. Med. 361, p. 888-898). IL-17A is a homodimeric molecule and after cleavage of a 23 amino acid signal peptide, it is secreted as a glycosylated, covalently-bound homodimer (NCBI Reference Sequence: NP_002181.1; UniProtK identifier: Q16552; SEQ ID: 10). F-endoglycosidase digestion shifts the apparent molecular weight of human IL-17A expressed by mammalian cells from 22 to 15 kDa on reducing SDS-PAGE, thus demonstrating that the cytokine is glycosylated (Fossiez F. et al. (1998) Int Rev Immunol. 16(5-6); p. 541-551).

The identification of Th17 cells as central mediators in chronic inflammatory processes and as principal pathogenic effectors in several types of autoimmunity conditions previously thought to be Th1-mediated promises new therapeutic approaches (Weaver T. et al. (2008) Annu. Rev. Immunol., 25, p. 821-852). Indeed, the pro-inflammatory cytokine IL-17 is mainly expressed by Th17 cells and is present at elevated levels in synovial fluid of patients with rheumatoid arthritis (RA) and has been shown to be involved in early RA development. In addition, IL-17 is a potent inducer of TNF-alpha and IL-1, the latter being mainly responsible for bone erosion and the very painful consequences for affected patients (Lubberts E. (2008) Cytokine, 41, p. 84-91). Furthermore, inappropriate or excessive production of IL-17 is associated with the pathology of various other diseases and disorders, such as osteoarthritis, loosening of bone implants, acute transplant rejection (Antonysamy et al., (1999) J. Immunol, 162, p. 577-584; van Kooten et al. (1998) J. Am. Soc. Nephroi., 9, p. 1526-1534), septicemia, septic or endotoxic shock, allergies, asthma (Molet et al. (2001) J. Allergy Clin. Immunol., 108, p. 430-438), bone loss, psoriasis (Teunissen et al. (1998) J. Invest. Dermatol, 111, p. 645-649), ischemia, systemic sclerosis (Kurasawa et al. (2000) Arthritis Rheum., 43, p. 2455-2463), stroke, and other inflammatory disorders.

Consequently, anti-IL-17 compounds have potential as anti-inflammatory agents, a therapeutic approach in line with a number of in vivo studies demonstrating that IL-17 neutralization reduces inflammatory processes such as arthritis. For example, the early neutralization of endogenous IL-17 by an IL-17 receptor-IgG1-Fc fusion protein starting after the immunization protocol during the initial phase of arthritis suppresses the onset of experimental arthritis (Lubberts et al. (2001) J. Immunol., 167, p. 1004-1013). Moreover, treatment with a neutralizing anti-IL-17 antibody in an animal model after the onset of collagen-induced arthritis reduced joint inflammation, cartilage destruction and bone erosion (Lubberts et al. (2004) Arthritis and Rheumatism, 50; 650-659). Histological analysis confirmed the suppression of joint inflammation, and systemic IL-6 levels were significantly decreased after treatment with an anti-IL-17 antibody. In contrast, systemic as well as local IL-17 overexpression using an adenoviral vector expressing murine IL-17 accelerated the onset of collagen-induced arthritis (CIA) and aggravated synovial inflammation at the site (Lubberts et al. (2001) J. Immunol., 167, p. 1004-1013 and Lubberts et al. (2002), Inflamm. Res. 51, p 102-104). More recently it could be demonstrated that the use of anti-IL-17 antibodies improved the clinical symptoms of psoriasis, rheumatoid arthritis and non-infectious uveitis (Leonardi C. et al. (2012) N. Engl. J. Med. 366, p. 1190-1199; Hueber W. et al. (2010) Sci Transl Med. 2(52): 52ra72).

Monospecific agents are widely used for the treatment of a variety of different diseases. Most of the marketed biologics are monospecific and therefore capable of interacting and interfering with a single target. However, complex diseases are often multifactorial in nature, and involve redundant or synergistic actions of disease mediators. Consequently, blockade of multiple, different pathological factors and pathways may result in improved therapeutic efficacy (Konterman R. E. (2012) mAbs, 4:2, p. 182-197).

Beside IL-17A, a further key molecule involved in the etiology of inflammatory diseases, autoimmune and bone-loss related diseases, in particular in the various forms of arthritis including rheumatoid arthritis is tumor necrosis factor (TNF). Several anti-TNF therapeutics have been approved for the treatment of rheumatoid arthritis, psoriasis, psoriatic arthritis, ankylosing spondylitis and Morbus Crohn, and are being tested in the clinic for other inflammatory conditions. There are currently five classes of biologics available for the treatment of inflammatory arthritis, each inhibiting a different aspect of the immune-driven inflammatory pathway (reviewed in Scott D. L. (2012) Clin Pharmacol Ther., 91(1), p. 31-43): (i) TNF inhibitors (adalimumab, etanercept, infliximab, certolizumab, golimumab), (ii) Interleukin-1 receptor antagonist (anakinra), (iii) B-cell inhibition (rituximab) (iv) T-cell costimulation inhibition (abatacept) and (v) Interleukin-6 inhibition (tocilizumab). Other approved biologics for the treatment of inflammatory conditions comprise canakinumab (anti-IL-1 beta) and ustekinumab (anti-IL-12/23) (Reichert J. M. (2012) mAbs, 4:3, p. 413-415). TNF binding molecules that are designed for therapeutic applications are also described in Tak and Kalden (2011) (Arthritis Research and Therapy, 13; 1-14).

Koenders et al. (2011) (Arthritis and Rheumatism, 63; 2329-2339) describe that the interplay between TNF and IL-17 triggers molecular mechanisms leading to irreversible cartilage destruction in an animal model of arthritis. Moreover, it has been found by the authors that the combination of a soluble interleukin-17 receptor and a TNF binding protein was more effective in the treatment of arthritis than either anti-cytokine treatment alone. The TNF binding molecule described in the publication of Koenders et al. (2011) is a dimerically linked PEGylated soluble p55 TNF receptor I. WO 2010/102251 describes binding proteins comprising first and second polypeptide chains, wherein the binding protein is capable of binding human IL-17 and TNF. Both polypeptide chains have a molecular architecture formed by antibody variable and constant domains. Several other bispecific and/or multispecific fusion proteins have been described in the literature (see review Konterman R. E. (2012) mAbs, 4:2, p. 182-197).

Fyn SH3-derived polypeptides are well known in the art and have been described e.g. in Grabulovski et al. (2007) JBC, 282, p. 3196-3204; WO 2008/022759; Bertschinger et al (2007) Protein Eng Des Sel 20(2):57-68; and Gebauer and Skerra (2009) Curr Opinion in Chemical Biology 13:245-255. The term "Fyn SH3-derived polypeptide", used interchangeably herein with the term "Fynomer", refers to a non-immunoglobulin-derived binding (poly)peptide (e.g. a so-called scaffold as described in Gebauer and Skerra (2009) Curr Opinion in Chemical Biology 13:245-255) derived from the human Fyn SH3 domain. The SH3 domain of the human Fyn kinase was successfully used as a scaffold to engineer proteins (Fyn SH3-derived binding proteins termed Fynomers) that bind with high affinity and specificity to different target proteins (WO 2008/022759, WO 2011/023685, Grabulovski D. et al., (2007) J Biol Chem 282, p. 3196-3204, Bertschinger J. et al. (2007) Protein Eng Des Sel, 20, p. 57-68, and Schlatter J. et al. (2012) mAbs, 4(4) p. 497-50).

WO 2011/023685 describes IL-17 inhibiting polypeptides ("Fynomers"), corresponding fusion proteins, compositions and medical uses thereof. These IL-17 inhibiting polypeptides have high specificity and high affinity for IL-17A. The technical problem underlying the present invention is the provision of further IL-17A inhibiting polypeptides and particular such IL-17A inhibiting polypeptides which are technically improved. This technical problem is solved by the embodiments characterized in the claims.

Accordingly, the present invention relates in a first embodiment to a polypeptide inhibiting the activity of glycosylated IL-17A, wherein the polypeptide comprises or consists of an amino acid sequence selected from the group consisting of:
(a) GVTLFVALYDY$(X^1)(X^2)(X^3)(X^4)(X^5)(X^6)$DLSFHKGEKFQILSTHEYEDWWEARSLTTGETGYIP SNYVAPVDSIQ (SEQ ID NO: 1), wherein amino acid positions $(X^1)$ to $(X^6)$ may be any amino acid sequence; and (b) an amino acid sequence which is at least 85% identical to the amino acid sequence of (a), wherein the identity determination excludes amino acid positions $(X^1)$ to $(X^6)$ and provided that the amino acid sequence STHEYE (SEQ ID NO: 2) in amino acid positions 31 to 36 of SEQ ID NO: 1 is conserved.

The invention also relates to fusion constructs, compositions and medical uses comprising said polypeptide.

The present invention relates in a second embodiment to a polypeptide binding glycosylated IL-17A and preferably inhibiting the activity thereof, wherein the polypeptide comprises or consists of an amino acid sequence selected from the group consisting of: (a) GVTLFVALYDY$(X^1)(X^2)(X^3)(X^4)(X^5)(X^6)$DLSFHKGEKFQIL STHEYEDWWEARSLTTGETGYIP SNYVAPVDSIQ (SEQ ID NO: 1), wherein amino acid positions $(X^1)$ to $(X^6)$ may be any amino acid sequence; and (b) an amino acid sequence which is at least 85% identical to the amino acid sequence of (a), wherein the identity determination excludes amino acid positions $(X^1)$ to $(X^6)$ and provided that the amino acid sequence STHEYE (SEQ ID NO: 2) in amino acid positions 31 to 36 of SEQ ID NO: 1 is conserved. The invention also relates to fusion constructs, compositions and medical uses comprising said polypeptide.

The following definitions, examples, preferred and independent embodiments refer both to the first and second embodiment of the invention.

The term "polypeptide" as used herein describes linear molecular chains of amino acids, including single chain proteins or their fragments, containing more than about 50 amino acids. Polypeptides may further form multimers, e.g. oligomers, consisting of at least two identical or different molecules. The corresponding higher order structures of such multimers are, correspondingly, termed homo- or heterodimers, homo- or heterotrimers etc. Furthermore, peptidomimetics of such polypeptides where amino acid(s) and/or peptide bond(s) have been replaced by functional analogs are also encompassed by the invention. Such functional analogues include all known amino acids other than the 20 gene-encoded amino acids, such as selenocysteine. The term "polypeptide" also refers to naturally modified polypeptides where the modification is effected e.g. by glycosylation, acetylation, phosphorylation and similar modifications which are well known in the art.

Also comprised by the present invention are fragments of the polypeptide of the invention which substantially retain binding to glycosylated IL-17A. In this regard it is preferred with increasing preference that the fragments comprise at least 30 amino acids, at least 35 amino acids, at least 40 amino acids, or at least 45 amino acids as long as the fragments contain less than about 55 amino acids. It is moreover preferred that in the fragment the amino acid positions corresponding to the RT- and src-loop as defined herein below are retained.

The term "polypeptide inhibiting the activity of glycosylated IL-17A" as used herein defines that the polypeptide has the capability to reduce or completely abolish the activity of glycosylated IL-17A, which activity is described herein above in detail. In this regard it is preferred that inhibiting glycosylated IL-17A activity means inhibiting the binding of glycosylated IL-17A to a type I cell surface receptor called IL-17R (interleukin 17 receptor). At least three variants of IL-17R, namely IL17RA, IL17RB, and IL17RC, are known in the art. In this regard, it is furthermore preferred with increasing preference that the polypeptide inhibits the activity of glycosylated IL-17A by at least 10%, at least 20%, at least 30%, at least 40%, at least 50%, at least 60%, at least 70%, at least 80%, at least 90%, at least 95%, or 100%. It is also preferred with increasing preference that $IC_{50}$ value for inhibition of glycosylated IL-17A of the polypeptides of the invention is 1000 nM or less, 500 nM or less, 400 nM or less, 300 nM or less, 200 nM or less, 100 nM or less, or 75 nM or less. In this regard it is preferred that the polypeptides of the invention specifically inhibits glycosylated IL-17A activity and thus does not inhibit other related proteins such as glycosylated IL-17B, IL-17C, IL-17D, IL-17E or IL-17F. The polypeptide of the invention inhibits the activity of glycosylated IL-17A. It is preferred that the polypeptide inhibits the activity of glycosylated and unglycosylated IL-17A. Hence, the above definitions apply mutatis mutandis to the inhibition of unglycosylated IL-17A.

It has to be understood that inhibiting glycosylated IL-17A activity also involves binding to glycosylated IL-17A. In this regard it is preferred that the binding to glycosylated IL-17A also leads to the inhibition of the activity of glycosylated IL-17A. The term "binding to glycosylated IL-17A" requires that the polypeptides or fragments of the invention form binding interactions (in vivo and/or in vitro) with glycosylated IL-17A. Preferably, the polypeptides of the invention bind to glycosylated IL-17A with a $K_D$ of $10^{-7}$ to $10^{-12}$ M, more preferably $10^{-8}$ to $10^{-12}$ M, most preferably $10^{-9}$ to $10^{-12}$ M. In this regard it is preferred that the polypeptides of the invention specifically bind to IL-17A and thus do not bind to other related proteins such as IL-17B, IL-17C, IL-17D, IL-17E or IL-17F. The polypeptide of the invention binds to glycosylated IL-17A. It is preferred that the polypeptide binds to glycosylated and unglycosylated IL-17A. Hence, the above definitions apply mutatis mutandis to the binding of unglycosylated IL-17A.

SEQ ID NO: 1 as recited herein above is derived from the amino acid sequence of the SH3 domain of the human Fyn kinase (SEQ ID NO: 20; aa 83-145 of Fyn kinase as reported by Kawakami et al. and Semba et al. in 1986). SEQ ID NO: 20 reads:

```
                                              (SEQ ID NO: 20)
GVTLFVALYDYEARTEDDLSFHKGEKFQILNSSEGDWWEARSLTTGETG
YIPSNYVAPVDSIQ.
```

In SEQ ID NO: 20 as shown above the sequences of the RT and the src loop are underlined and double-underlined, respectively. Grabulovski et al. (2007) JBC, 282, p. 3196-3204 investigated the influence of mutations in the RT and src loops of Fyn SH3 domains and demonstrated that mutations in both loops which are adjacent to the hydrophobic surface could determine the ability of this domain to participate in intermolecular associations. Moreover, EP 2054432 shows that mutations in and adjacent to the RT and/or the src loop determine the binding specificity of an SH3 domain. The amino acid sequence of Fyn SH3 is fully conserved among man, mouse, rat and monkey (gibbon). Chicken Fyn SH3 differs in one, the one of *Xenopus laevis* in two amino acid positions from the corresponding human domain. Just as other SH3 domains the Fyn SH3 is composed of two antiparallel β-sheets and contains two flexible loops (called RT and src-loops) in order to interact with other proteins.

In more detail, SEQ ID NO: 1 is a sequence resulting from an alignment of SEQ ID NOs: 3 to 9 (cf. FIG. 8). As it is evident from FIG. 8, positions ($X^1$) to ($X^6$) of SEQ ID NO: 1 correspond to the RT-loop of the Fyn Kinase SH3 domain of SEQ ID NO: 20. In this regard, it is preferred that amino acid positions ($X^1$) to ($X^6$) of the polypeptide of the invention do not have the sequence EARTED (SEQ ID NO: 19). As it is furthermore evident from FIG. 8, the positions corresponding to the src-loop of the Fyn Kinase SH3 domain of SEQ ID NO: 20, namely the sequence "STHEYE" (underlined in SEQ ID NO: 1 as shown herein above) are conserved among SEQ ID NOs: 3 to 9. The amino acid positions within the RT and src-loop determine the binding specificity to the glycosylated IL-17A.

In accordance with the present invention, the term "percent (%) sequence identity" describes the number of matches ("hits") of identical nucleotides/amino acids of two or more aligned nucleic acid or amino acid sequences as compared to the number of nucleotides or amino acid residues making up the overall length of the template nucleic acid or amino acid sequences. In other terms, using an alignment, for two or more sequences or subsequences the percentage of amino acid residues or nucleotides that are the same (e.g. 85%, 90% or 95% identity) may be determined, when the (sub)sequences are compared and aligned for maximum correspondence over a window of comparison, or over a designated region as measured using a sequence comparison algorithm as known in the art, or when manually aligned and visually inspected. The sequences which are compared to determine sequence identity may thus differ by substitution(s), addition(s) or deletion(s) of nucleotides or amino acids. This definition also applies to the complement of a test sequence.

The skilled person is also aware of suitable programs to align nucleic acid sequences. The percentage sequence identity of polypeptide sequences can, for example, be determined with programmes as the above explained programmes CLUSTLAW, FASTA and BLAST. Preferably the BLAST programme is used, namely the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402).

With regard to the sequence identity as recited in item (b) herein above, it is preferred with increasing preference that the sequence identity is at least 90%, at least 95%, or at least 98%.

The phrase "the identity determination excludes amino acid positions ($X^1$) to ($X^6$)" as used herein specifies that the calculation of the sequence identity with regard to SEQ ID NO. 1 does not take into account amino acid positions ($X^1$) to ($X^6$) but is confined to the remainder of the 58 amino acids positions of SEQ ID NO: 1. The condition "provided that the amino acid sequence STHEYE (SEQ ID NO: 2) in amino acid positions 31 to 36 of SEQ ID NO: 1 is conserved" as used herein specifies that no amino acids changes may be introduced into amino acid positions 31 to 36 of SEQ ID NO: 1. In other terms, the amino acid positions corresponding to amino acids position 31 to 36 of SEQ ID NO: 1 have the sequence STHEYE (SEQ ID NO: 2) in all polypeptides falling under the ambit of the first embodiment of the invention and the preferred examples thereof.

In this regard it is preferred that the amino acid positions corresponding to amino acids position 31 to 37 of SEQ ID NO: 1 have the sequence STHEYED (SEQ ID NO: 18) in all polypeptides falling under the ambit of the first embodiment of the invention and the preferred examples thereof. In other words, it is preferred with respect to the first embodiment of the invention and the preferred examples thereof that the condition that the amino acid sequence STHEYED (SEQ ID NO: 18) in amino acid positions 31 to 37 of SEQ ID NO: 1 is conserved is met.

Any amino acid substitution in SEQ ID NO: 1 is preferably a conservative amino acid substitution. A conservative substitution specifies the replacement of an amino acid with another amino acid having a chemical property similar to the amino acid that is replaced. Preferably, the conservative substitution as referred to herein is a substitution selected from the group consisting of: (i) a substitution of a basic amino acid with a different basic amino acid; (ii) a substitution of an acidic amino acid with a different acidic amino acid; (iii) a substitution of an aromatic amino acid with a different aromatic amino acid; (iv) a substitution of a non-polar, aliphatic amino acid with a different non-polar, aliphatic amino acid; and (v) a substitution of a polar, uncharged amino acid with a different polar, uncharged amino acid. Basic amino acids are arginine, histidine, and lysine. Acidic amino acids are aspartate or glutamate. Aromatic amino acids are phenylalanine, tyrosine and tryptophane. Non-polar, aliphatic amino acids are glycine, alanine, valine, leucine, methionine, isoleucine and proline. Polar, uncharged amino acids are serine, threonine, cysteine, asparagine and glutamine. In contrast to a conservative amino acid substitution, a non-conservative amino acid substitution is the exchange of one amino acid with any amino acid that does not fall under the above-outlined conservative substitutions (i) through (v).

The term "IL-17A" or "interleukin 17A" (previously named CTLA-8, and also referred to herein and in the art simply as "IL-17" or "interleukin 17" since it is the founding member of the IL17 family) designates a potent pro-inflammatory cytokine produced by activated memory T cells (Gurney and Aggarwal (2002), "IL-17: prototype member of an emerging cytokine family", J. Leukoc. Biol. 71(1):1-8). In more detail, IL-17A is a cytokine that acts as a potent mediator in delayed-type reactions by increasing chemokine production in various tissues to recruit monocytes and neutrophils to the site of inflammation, similar to Interferon gamma. IL-17A is produced by T-helper cells and is induced by IL-23 which results in destructive tissue damage in delayed-type reactions. Interleukin 17A as a family functions as a proinflammatory cytokine that responds to the invasion of the immune system by extracellular pathogens and induces destruction of the pathogen's cellular matrix. Interleukin 17A acts synergistically with tumor necrosis factor and interleukin-1. Human IL-17A is a 155-amino acid protein, preferably comprising or consisting of SEQ ID NO 10 that is a disulfide-linked, homodimeric, secreted glycoprotein with a molecular mass of 35 kDa. Each subunit of the homodimer is approximately 15-20 kDa. The structure of IL-17A consists of a signal peptide of 23 amino acids (aa) followed by a 132-aa chain region characteristic of the IL-17 family. An N-linked glycosylation site on the protein was first identified after purification of the protein revealed two bands, one at 15 KDa and another at 20 KDa. As mentioned, IL17 as initially identified was designated IL-17A to indicate that it is the founding member of this cytokine family. In addition to IL-17A, members of the IL-17 family include IL-17B, IL-17C, IL-17D, IL-17E (also called IL-25), and IL-17F. The IL-17 family is thought to represent a distinct signaling system that appears to have been highly conserved across vertebrate evolution. All members of the IL-17 family have a similar protein structure, with four highly conserved cysteine residues critical to their 3-dimensional shape, yet they have no sequence similarity to any other known cytokines.

The IL-17A inhibiting polypeptides disclosed herein surprisingly have a high specificity and high affinity for unglycosylated IL-17A as well as glycosylated IL-17A. In particular, SEQ ID NOs 3 to 9 of the invention are able to completely inhibit glycosylated IL-17A with similar potencies as compared to non-glycosylated IL-17A (see Example 3). This is an advantageous property as compared to the Fyn SH3-derived IL-17A-binding polypeptides that are known from WO 2011/023685. The Fyn SH3-derived IL-17A-binding polypeptides described in WO 2011/023685 either do not completely inhibit glycosylated IL-17A even at high concentrations and/ or show large differences in inhibition potency ($IC_{50}$ values) between glycosylated and non-glycosylated IL-17A (see Example 3 and FIG. 3). As discussed herein above, IL-17A is secreted in vivo as a glycosylated, covalently-bound homodimer. The novel IL-17A-binding molecules disclosed herein—having the advantage of binding to and inhibiting glycosylated IL-17A—are therefore particularly suitable for applications requiring the detection or binding to IL-17A in vivo, where it is predominately present as a glycosylated protein. Such applications are, for example, diagnostic and medical treatments, preferably the formulation of medicaments for treating and/or preventing IL-17A-mediated diseases.

The examples herein below show that the amino acids listed for amino acid positions ($X^1$) to ($X^6$) confer binding specificity to glycosylated IL-17A, in particular to the glycosylated IL-17A having SEQ ID NO: 10. In more detail, the sequence alignment of SEQ ID NOs 3 to 9 of the invention in FIG. 8 shows that amino acids positions ($X^1$) to ($X^6$) are selected from ($X^1$) is A, K, S, D or E; ($X^2$) is N, Q, A, K, S or R; ($X^3$) is H, K, R, L or V; ($X^4$) is G or S; ($X^5$) is H, Q, A, W, V or N; and ($X^6$) is R, L or S in SEQ ID NOs 3 to 9. Therefore, it can be expected that also other amino acid sequences selected from ($X^1$) to ($X^6$) as defined above than the specific amino acid combinations for ($X^1$) to ($X^6$) as present in SEQ ID NOs 3 to 9 confer binding specificity to glycosylated IL17A.

In a preferred embodiment of the invention amino acid positions ($X^1$) to ($X^6$) of the polypeptide of the invention are thus selected from ($X^1$) being A, K, S, D or E; ($X^2$) being N, Q, A, K, S or R; ($X^3$) being H, K, R, L or V; ($X^4$) being G or S; ($X^5$) being H, Q, A, W, V or N; and ($X^6$) being R, L or S (see SEQ ID NO: 21).

Also encompassed by the present invention are conservative amino acid substitutions of ($X^1$) being A, K, S, D or E; ($X^2$) being N, Q, A, K, S or R; ($X^3$) being H, K, R, L or V; ($X^4$) being G or S; ($X^5$) being H, Q, A, W, V or N; and ($X^6$) being R, L or S.

It is particularly preferred that amino acid positions ($X^1$) to ($X^6$) of the polypeptide of the invention are selected from ($X^1$) being S or E; ($X^2$) being A or S; ($X^3$) being R or V; ($X^4$) being G or S; ($X^5$) being Q or V; and ($X^6$) being L or S. These amino acids correspond to positions ($X^1$) to ($X^6$) in SEQ ID NOs 5 and 7, respectively. It is most preferred that amino acid positions ($X^1$) to ($X^6$) of the polypeptide of the invention are ($X^1$) being S; ($X^2$) A; ($X^3$) being R; ($X^4$) being G; ($X^5$) being Q; and ($X^6$) being L. These amino acids correspond to positions ($X^1$) to ($X^6$) in SEQ ID NO: 5.

In accordance with a polypeptide according to item (b) of the first polypeptide, not only amino acid positions ($X^1$) to ($X^6$) may differ between the amino acid sequence of SEQ ID NO: 1 (or the SEQ ID NOs 3 to 9) but also additional amino acids positions which are not within the RT- and/or src-loop (having the sequence STHEYE (SEQ ID NO: 2) in accordance with the invention) of the SH3 domain of the Fyn kinase (SEQ ID NO: 20). It is believed that amino acids differences in these positions are not essential to the binding specificity of SEQ ID NOs. 3 to 9. Thus, these amino acids positions may be exchanged or deleted, or further amino acids may be added, without substantially interfering with the binding specificity to glycosylated IL17A. If amino acids are exchanged, conservative exchanges are preferred.

In a more preferred embodiment the polypeptide of the invention comprises or consists of an amino acid sequence selected from the group consisting of any one of SEQ ID NOs 3 to 9.

As it is shown in the examples herein below, SEQ ID NOs 3 to 9 were found to bind to and inhibit unglycosylated as well as glycosylated IL-17A having SEQ ID NO: 10. In more detail, it was surprisingly found that the Fyn SH3-derived IL-17A-binding polypeptides of SEQ ID NOs 3 to 9 are able to completely inhibit glycosylated IL-17A with similar potencies as compared to non-glycosylated IL-17A. This is an advantageous property as compared to the Fyn SH3-derived IL-17A-binding polypeptides that are described in WO 2011/023685 (see comparative data in Example 3).

Among SEQ ID NOs 3 to 9 a preference is given to SEQ ID NOs 5 and 7. SEQ ID NOs 5 and 7 have been used to generate the fusion constructs and constructs described herein in Example 4. The obtained fusion constructs and constructs were particularly useful, because they are stable, monomeric, soluble and display excellent biophyiscal and drug-like properties. Furthermore, the fusion of SEQ ID NOs 5 and 7 to further compounds did not effect the excellent binding to glycosylated IL-17A.

As it is well known, minor changes in an amino acid sequence such as deletion, addition or substitution of one, a few or even several amino acids may lead to a mutant form of the original protein which has substantially identical properties. Therefore, as regards SEQ ID NOs 3 to 9 also encompassed by the present invention is a polypeptide comprising an amino acid sequence which is at least 85%, preferably at least 90%, more preferably at least 95% and most preferred at least 98% identical to any one of SEQ ID NOs 3 to 9, provided that the amino acid sequence STHEYE (SEQ ID NO: 2) in amino acid positions 31 to 36 of SEQ ID NO: 1 is conserved. If amino acids are exchanged, conservative exchanges are preferred.

It is furthermore preferred in accordance with the invention that the IL-17A comprises or consists of the amino acids sequence of SEQ ID NO: 10.

As it is evident from the examples herein below, the human IL-17A having SEQ ID NO: 10 has been used as the target protein in order to identify the polypeptides having SEQ ID NOs 3 to 9. The first 23 amino acid of SEQ ID NO: 10 are the signal peptide. It is therefore particularly preferred that the polypeptide of the invention binds to glycosylated IL-17A within amino acid positions 24 to 155 of SEQ ID NO: 10.

In another embodiment the present invention relates to a fusion construct comprising the polypeptide of the invention fused to a further compound.

A "fusion construct" has used herein defines the fusion of the polypeptide of the invention to a further compound. The compound may either be a proteinous compound or a non-proteinous compound. In the case the compound is a proteinous compound (e.g. a cytokine or chemokine as described herein below), the fusion construct may also be designated as fusion protein. The term "fusion protein" as used herein is in general terms directed to a polypeptide construct generated through the joining and expression of two or more genes which code for separate polypeptides. In other words, translation of this fusion gene results in a single polypeptide with functional properties derived from each of the original polypeptides. The polypeptides may either be directly fused or via a linker, i.e. a short peptide sequence. In general, fusion proteins are generated artificially by recombinant DNA technology well know to the skilled person (e.g. Alberts et al., Molecular Biology of the Cell, 4$^{th}$ ed. Garland Science, p. 518-519). However, polypeptides and fusion proteins of the invention may be prepared by any of the many conventional and well known techniques such as plain organic synthetic strategies, solid phase-assisted synthesis techniques or by commercially available automated synthesizers. Fusion proteins may be used in biological research or therapeutics.

Examples of non-proteinous compounds as the further compound are, for example, small organic molecules, such as polyethylenglycol (PEG) or Alexa Fluor, or radionuclides. Further specific examples of non-proteinous further compounds are discussed herein below.

In accordance with a preferred embodiment the further compound is a pharmaceutically active compound, a prodrug, a pharmaceutically-acceptable carrier, a diagnostically active compound, a cell penetrating enhancer, and/or a compound modulating serum half-life.

A pharmaceutically active compound is a compound having a biologically activity upon administration to a subject, which brings about a beneficial effect for the subject. A prodrug is a compound that is administered in an inactive (or less than fully active) form to a subject, and is subsequently converted to a pharmaceutically active or pharmaceutically fully active compound through metabolic processes in the subject. The pharmaceutically (fully) active compound is preferably a compound suitable for the treatment of prevention of any of the specific diseases defined herein below.

A diagnostically active compound is a compound having an activity upon administration to a subject, which allows to determine or identify a possible disease or disorder. Examples of diagnostically active compounds include detectable markers such as fluorescent dyes, radionuclides or contrast agents for medical imaging. Specific examples of fluorescent dyes, radionuclides and contrast agents for medical imaging are described herein below. A diagnostically active compound fused to a polypeptide of the invention can in particular be used to determine or identify any one of the specific diseases defined herein below which have in common that their origin and/or symptom(s) are IL-17A- and/or Th-17-related. The sides of such disease can be detected or identified by the polypeptide of the invention fused to the diagnostically active compound of the invention.

A cell penetrating enhancer is a compound facilitating the delivery of the polypeptide of the invention into a (in vitro, ex vivo or in vivo) cell.

A compound modulating serum half-life is a compound which allows for extending the in vivo half-life of the polypeptides of the invention, in particular in the blood circulation system. The component modulating serum half-life is preferably polyethylene glycol (PEG).

A pharmaceutically-acceptable carrier is a compound that improves the delivery and/or the effectiveness of the polypeptide of the invention upon administration to a subject. Suitable pharmaceutically-acceptable carriers are well known in the art and include, for example, stabilizers, antioxidants, pH-regulating substances, etc.

In accordance with another preferred embodiment the further compound of the invention is selected from the group consisting of (a) a fluorescent dye, (b) a photosensitizer, (c) a radionuclide, (d) a contrast agent for medical imaging, (e) a cytokine, (f) a toxic compound, (g) a chemokine, (h) a procoagulant factor, (i) an enzyme for pro-drug activation, (k) an albumin binder, (l) an albumin, (m) an IgG binder, or (n) polyethylene glycol.

The fluorescent dye is preferably a component selected from Alexa Fluor or Cy dyes.

The photosensitizer is preferably phototoxic red fluorescent protein KillerRed or haematoporphyrin.

The radionuclide is preferably either selected from the group of gamma-emitting isotopes, more preferably $^{99m}$Tc, $^{123}$I, $^{111}$In, and/or from the group of positron emitters, more preferably $^{18}$F, $^{64}$Cu, $^{68}$Ga, $^{86}$Y, $^{124}$I, and/or from the group of beta-emitter, more preferably $^{131}$I, $^{90}$Y, $^{177}$Lu, $^{67}$Cu, or from the group of alpha-emitter, preferably $^{213}$Bi, $^{211}$At.

A contrast agent as used herein is a substance used to enhance the contrast of structures or fluids within the body in medical imaging. Common contrast agents work based on X-ray attenuation and magnetic resonance signal enhancement.

The cytokine is preferably selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1beta. As it is well-known in the art, cytokines may favour a pro-inflammatory or an anti-inflammatory response of the immune system. Thus, depending on the disease to be treated either fusion constructs with a pro-inflammatory or an anti-inflammatory cytokine may be favored. For example, for the treatment of inflammatory diseases in general fusion constructs comprising anti-inflammatory cytokines are preferred, whereas for the treatment of cancer in general fusion constructs comprising pro-inflammatory cytokines are preferred.

The toxic compound is preferably a small organic compound or a polypeptide, more preferably a toxic compound selected from the group consisting of calicheamicin, maytansinoid, neocarzinostatin, esperamicin, dynemicin, kedarcidin, maduropeptin, doxorubicin, daunorubicin, auristatin, Ricin-A chain, modeccin, truncated *Pseudomonas* exotoxin A, diphtheria toxin and recombinant gelonin.

The chemokine is preferably selected from the group consisting of IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, eotaxin, Eotaxin-2, I-309, MPIF-1, 6Ckine, CTACK, MEC, lymphotactin and fractalkine.

The pro-coagulant factor is preferably the tissue factor (TF) or cancer procoagulant (CP).

The enzyme for pro-drug activation is preferably an enzyme selected from the group consisting of carboxy-peptidases, glucuronidases and glucosidases.

Examples of an albumin binder, and an IgG binder are described in Gebauer and Skerra (2009), 13:245-255. Accordingly, preferred examples of albumin binders and an IgG binders are human single Ig domains (dubbled Albumin Dab), nanobodies, naturally occurring albumin binding domain (ABD) derived from streptococcal protein G, and a domain that binds to IgG. Such fusion constructs, for example, increase the half life of the polypeptide of the invention upon administration to a patient, in particular in the blood circulation system.

In accordance with another preferred embodiment the further compound of the invention consists of or comprises an antibody light chain, an antibody heavy chain, an $F_c$ domain of an antibody, an antibody, or a combination thereof.

The term "antibody" includes monoclonal antibodies, polyclonal antibodies, single chain antibodies, or fragments thereof that specifically bind said peptide or polypeptide, also including bispecific antibodies, synthetic antibodies, antibody fragments other than heavy and light chains, such as Fab, a F(ab$_2$)', Fv or scFv fragments etc., or a chemically modified derivative of any of these. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

The antibody may be a humanized antibody. The term "humanized antibody" means, in accordance with the present invention, an antibody of non-human origin, whose protein sequences has been modified to increase its similarity to antibody variants produced naturally in humans. Creation of a humanized antibody may be accomplished, for example, by inserting the appropriate CDR coding segments (responsible for the desired binding properties), such as CDR 3 and preferably all 6 CDRs, into a human antibody "scaffold". Methods for the production of humanized antibodies are described in, e.g., EP-A1 0 239 400 and WO 90/07861.

The term "antibody light chain" designates the small polypeptide subunit of an antibody while the term "antibody heavy chain" designates the large polypeptide subunit of an antibody. A typical antibody is composed of two immunoglobulin (Ig) heavy chains and two Ig light chains. Each light chain is composed of two tandem immunoglobulin domains; one constant ($C_L$) domain and one variable domain ($V_L$) that is important for binding antigen. The heavy chain determines the class or isotype of an antibody. Each heavy chain has two regions, namely a constant region (which is the same for all immunoglobulins of the same class but differs between classes) and a variable region that differs between different B cells, but is the same for all immunoglobulins produced by the same B cell or B cell clone. The variable domain of any heavy chain is composed of a single immunoglobulin domain.

A "functional Fc domain" of an antibody is a term well known to the skilled artisan and defined on the basis of papain cleavage of antibodies. Depending on the amino acid sequence of the constant region of their heavy chains, immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called [alpha], [delta], [epsilon], [gamma], and [mu], respectively. The functional Fc domain of an antibody is directly involved in ADCC (antibody-dependent cell-mediated cytotoxicity) and CDC (complement-dependent cytotoxicity) based on complement activation, C1q binding and Fc receptor binding. The four human IgG isotypes bind different receptors, such as the neonatal Fc receptor, the activating Fc gamma receptors, FcγRI, FcγRIIa, and FcγRIIIa, the inhibitory receptor FcγRIIb, and C1q with different affinities, yielding very different activities. It is known that the affinities to activating and inhibiting receptors of an Fc domain of a human antibody can be engineered and modified (see Strohl W. (2009) Curr Opin Biotechnol, 20, p. 685-691).

Preferably, the Fc domain is one or more human functional Fc domains which allow(s) for extending the in vivo half-life of the polypeptides of the invention and some of which direct a mammal's immune response to a site of specific target binding of the inventive polypeptide component of the fusion protein, e.g. in therapeutic, prophylactic and/or diagnostic applications as described herein below. More preferably such a human functional Fc domain is of an IgG1 antibody The polypeptides of the invention can be fused either to the N- or C-terminus of one or more functional Fc domains or to both the N- and the C-terminus of one or more Fc domains. It is preferred that the fusion proteins of the invention comprise multimers, preferably tetramers, trimers or most preferably dimers of the polypeptides of the invention fused to at least one side, preferably to the N-terminus of one or more, preferably one Fc domain.

In a more preferred embodiment of the present invention, the Fc domain is one or more engineered human functional Fc domains of an IgG1 with activating or silenced effector functions, preferably one or more engineered human functional Fc domains of an IgG1 with silenced effector functions, and even more preferably one or more engineered human functional Fc domains of an IgG1 with silenced effector functions with a mutation in L234 and L235, numbering according to EU index of Kabat (see Johnson G. and Wu T. T. (2000) Nucleic Acids Res. 28, p. 214-218), and most preferred with the mutation L234A and L235A.

The antibody in the fusion construct of the the invention preferably specifically binds to TNFα. The term "specifically binds to" refers to those cases where TNFα is bound with equilibrium binding constant $K_D$ which is by a factor 2 smaller, preferably by a factor 5 or a factor 10 smaller as compared to the equilibrium binding constant observed for the binding of the fusion construct of the invention to an unrelated protein, such unrelated protein being not a member of the TNF family or a different member of the TNF family such as TNFβ.

In accordance with another preferred embodiment of the fusion construct of the the invention, the polypeptide of the invention is located downstream of the C-terminus of said further compound consisting of or comprising an antibody light chain, an antibody heavy chain, an $F_c$ domain of an antibody, an antibody, or a combination thereof.

Such further compound may either be directly fused to the polypeptide or via a linker. Accordingly, the fusion construct may be (directly) fused to the C-terminus of the further compound, more specifically by the formation of a peptide bond between the carboxy group of the C-terminal amino acid of and the amino group of the N-terminal amino acid, or may be connected to the C-terminus of the further compound chain via a linker.

Suitable linkers are at the skilled person's disposal. The linker according to the invention is preferably selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. Preference is also given to peptidic linkers, more specifically to oligopeptides having a length from 2 to 30 amino acids. Use of a single amino acid is also deliberately envisaged. Preferred length ranges are from 5 to 15 amino acids. Other preferred lengths are 3, 4, 6, 7, 8, 9, 10, 11, 12, 13, 14, 16, 17, 18, 19 or 20 amino acids.

Particularly preferred are linkers which are peptides which consist of at least 50%, at least 60%, at least 70%, at least 80%, at least 90% or 100% of small amino acids such as glycine, serine and alanine. Particularly preferred are linkers consisting of glycines and serines only. Most preferred are the linkers of SEQ ID NOs: 13 to 15 with special preference given to a linker being a peptide consisting of the sequence of SEQ ID NO: 15.

In accordance with another preferred embodiment of the fusion construct of the the invention, the further compound comprises or consists of an antibody light chain comprising or consisting of SEQ ID NO: 11.

SEQ ID NO: 11 is the light chain of an anti-TNFα antibody. It has to be understood that also SEQ ID NO: 11 may either be directly fused to the polypeptide or the invention or via a linker. Accordingly, the fusion construct may be (directly) fused to the C-terminus of the further compound, more specifically by the formation of a peptide bond between the carboxy group of the C-terminal amino acid of and the amino group of the N-terminal amino acid, or may be connected to the C-terminus of the further compound chain via a linker. Preferred linkers comprise or consist of a sequence selected from the group consisting of SEQ ID NOs: 13 to 15, wherein SEQ ID NO: 15 is most preferred. Particularly preferred examples of the fusion construct in accordance with this embodiment comprise or consist of SEQ ID NOs 16 or 17, wherein SEQ ID NO: 16 is most preferred.

In a further embodiment the present invention relates to a construct comprising or consisting of at least one copy, preferably two copies of the fusion construct comprising or consisting of an antibody light chain comprising or consisting of SEQ ID NO: 11 and at least one copy, preferably two copies of the antibody heavy chain of SEQ ID NO: 12.

SEQ ID NO: 12 is the heavy chain of an anti-TNFα antibody. Hence, the construct according to this embodiment at least comprises the polypeptide binding to glycosylated IL-17A of the invention, the light chain of an anti-TNFα antibody (SEQ ID NO: 11) and the heavy chain of an anti-TNFα antibody (SEQ ID NO: 12), wherein the polypeptide binding to glycosylated IL-17A of the invention and the light chain of an anti-TNFα antibody form the fusion. It is preferred that the number of copies of the light and the heavy chain in the construct of the invention is the same. The light chain component of the antibody, when brought together with the heavy chain component of the antibody, provides for the formation of an antigen binding site which site recognizes TNFα. In case the construct comprises each two copies of the light chain of an anti-TNFα antibody (SEQ ID NO: 11) and the heavy chain of an anti-TNFα antibody (SEQ ID NO: 12), the construct preferably comprises a complete anti-TNFα antibody, wherein each light chain of said antibody is directly fused or fused via a linker to the polypeptide of the invention. Preferred examples of such constructs are described in Example 4 and shown in Table 4 herein below.

In accordance with a preferred embodiment the present invention relates to a construct comprising or consisting of at least one copy, preferably two copies of the fusion construct comprising or consisting of SEQ ID NO: 16 or 17 (wherein SEQ ID NO: 16 is preferred) and at least one copy, preferably two copies of the antibody heavy chain of SEQ ID NO: 12.

It is preferred that this construct comprises or consists of two copies of the fusion construct comprising or consisting of SEQ ID NO: 16 or 17 (wherein SEQ ID NO: 16 is preferred) and two copies of the antibody heavy chain of SEQ ID NO: 12. Such construct may thus comprise a complete anti-TNFα antibody.

Within the construct of the invention it is preferred that the polypeptide of the invention is located downstream of the C-terminus of the light chain comprising or consisting of SEQ ID NO: 11.

The construct of the invention is capable of concomitantly binding two target molecules, namely glycosylated interleukin-17A on the one hand and TNFα on the other hand. The construct comprises a functional glycosylated IL-17A binding site owing to the presence of the polypeptide of the invention.

The construct according to the present invention may be obtained by bringing together, under suitable conditions, said fusion protein and said antibody heavy chain. The skilled person is aware of suitable conditions. Such bringing together under suitable conditions provides for the non-covalent assembly triggered by the interactions between the antibody light chain as comprised in said fusion protein and said antibody heavy chain. Preferably, disulfide bonds as they are commonly found in antibodies are present in the construct of the invention. Disulfide bonds are typically present in the proximity of the hinge region and connect two heavy chains and/or a light chain and a heavy chain.

The present invention furthermore relates to a nucleic acid molecule encoding the polypeptide of the invention, or the fusion construct of the invention, or one or more nucleic acid molecules encoding the construct of the invention.

The one or more nucleic acid molecules encoding the construct of the invention may be, for example, two nucleic acid molecule wherein one nucleic acid molecule encodes the fusion construct of the invention and the other nucleic acid molecule the heavy chain of an antibody.

Nucleic acid molecules, in accordance with the present invention, include DNA, such as cDNA, and mRNA. Further included are nucleic acid mimicking molecules known in the art such as synthetic or semisynthetic derivatives of DNA or RNA and mixed polymers, both sense and antisense strands. They may contain additional non-natural or derivatized nucleotide bases, as will be readily appreciated by those skilled in the art. In a preferred embodiment the polynucleotide or the nucleic acid molecule(s) is/are DNA. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see, for example, Braasch and Corey, Chemistry & Biology 8, 1-7 (2001)). LNA is an RNA derivative in which the ribose ring is constrained by a methylene linkage between the 2'-oxygen and the 4'-carbon.

For the purposes of the present invention, a peptide nucleic acid (PNA) is a polyamide type of DNA analog. The monomeric units for the corresponding derivatives of adenine, guanine, thymine and cytosine are available commercially (for example from Perceptive Biosystems). PNA is a synthetic DNA-mimic with an amide backbone in place of the sugar-phosphate backbone of DNA or RNA. As a consequence, certain components of DNA, such as phosphorus, phosphorus oxides, or deoxyribose derivatives, are not present in PNAs.

PNA chimera according to the present invention are molecules comprising one or more PNA portions. The remainder of the chimeric molecule may comprise one or more DNA portions (PNA-DNA chimera) or one or more (poly)peptide portions (peptide-PNA chimera). Peptide-DNA chimera according to the invention are molecules comprising one or more (poly)peptide portions and one or more DNA portions. Molecules comprising PNA, peptide and DNA portions are envisaged as well. The length of a portion of a chimeric molecule may range from 1 to n−1 bases, equivalents thereof or amino acids, wherein "n" is the total number of bases, equivalents thereof and amino acids of the entire molecule.

The term "derivatives" in conjunction with the above described PNAs, (poly)peptides, PNA chimera and peptide-DNA chimera relates to molecules wherein these molecules comprise one or more further groups or substituents different from PNA, (poly)peptides and DNA. All groups or substituents known in the art and used for the synthesis of these molecules, such as protection groups, and/or for applications involving these molecules, such as labels and (cleavable) linkers are envisaged.

In those embodiments where the nucleic acid molecule comprises (rather than have) the recited sequence, additional nucleotides extend over the specific sequence either on the 5' end or the 3' end or both. Those additional sequence may be of heterologous or homologous nature and may comprise stretches of about 50 to 500 nucleotides although higher or lower values are not excluded. In the case of homologous sequences, those embodiments do not include complete genomes and are generally confined to about 1500 additional nucleotides at the 5' and/or the 3' end.

Additional heterologous sequences may include heterologous promoters which are operatively linked to the coding sequences of above molecules. Hence, preferably the nucleic acid molecule is operably linked to a promoter, and more preferably linked to a promoter selected from the group of prokaryotic promoters consisting of T5 promoter/lac operator element, T7 promotor/lac operator element, or from the group of eukaryotic promoters consisting of hEF1-HTLV, CMV enh/hFerL promoter.

The present invention also relates to one or more vectors comprising one or more nucleic acid molecule of the invention as well as one or more host cells comprising the one or more nucleic acid molecule of the invention or the one or more vectors of the invention.

The vectors and isolated cells, in particular host cells, may be any conventional type that suits the purpose, e.g. production of polypeptides, fusion constructs and/or constructs of the invention, and/or therapeutically useful vectors and host cells, e.g. for gene therapy. The skilled person will be able to select those nucleic acid molecules, vectors and host cells from an abundant prior art and confirm their particular suitability for the desired purpose by routine methods and without undue burden.

It is also preferred that the one or more vectors of the invention i comprise one or more nucleic acids of the invention and are preferably capable of producing a polypeptide or fusion protein of the invention. Preferably such vectors are selected from the group consisting of pQE vectors, pET vectors, pFUSE vectors, pUC vectors, YAC vectors, phagemid vectors, phage vectors, vectors used for gene therapy such as retroviruses, adenoviruses, adeno-associated viruses. For vector modification techniques, see Sambrook and Russel (2001), loc. cit. Generally, vectors can contain one or more origin of replication (ori) and inheritance systems for cloning or expression, one or more markers for selection in the host, e. g., antibiotic resistance, and one or more expression cassettes. Suitable origins of replication (ori) include, for example, the Col E1, the SV40 viral and the M 13 origins of replication.

The one or more nucleic acid molecules of the present invention may also be inserted into one or more vectors such that a translational fusion with another nucleic acid molecule is generated. The other nucleic acid molecule preferably encodes the light and/or heavy chain of an anti-TNFα antibody and/or a linker, preferred examples of which are described herein above.

The one or more host cells may be produced by introducing the one or more nucleic acid molecules or one or more vectors of the invention into the one or more host cells which upon their presence mediates the expression of the polypeptides encoded by said nucleic acid molecules or vectors. The host cells are preferably isolated host cell, meaning that the cells are not within the context of a living organism. The host may be any prokaryotic or eukaryotic cell. A suitable eukaryotic host may be a mammalian cell, an amphibian cell, a fish cell, an insect cell, a fungal cell or a plant cell. A eukaryotic cell may be an insect cell such as a *Spodoptera frugiperda* cell, a yeast cell such as a *Saccharomyces cerevisiae* or *Pichia pastoris* cell, a fungal cell such as an *Aspergillus* cell or a vertebrate cell. In the latter regard, it is preferred that the cell is a mammalian cell such a human cell. The cell may be a part of a cell line.

Suitable prokaryotes/bacteria are those generally used for cloning like *E. coli* (e.g., *E coli* strains HB101, DH5a, XL1 Blue, Y1090 and JM101), *Salmonella typhimurium, Serratia marcescens, Burkholderia glumae, Pseudomonas putida, Pseudomonas fluorescens, Pseudomonas stutzeri, Streptomyces lividans, Lactococcus lactis, Mycobacterium smegmatis* or *Bacillus subtilis*. A preferred example for a host cell to be genetically engineered with the nucleic acid molecule or vector of the invention is *E. coli*.

The present invention is also directed to a pharmaceutical or diagnostic composition comprising the polypeptide of the invention, the fusion construct of the invention, the construct of the invention, one or more nucleic acid molecules of the invention, one or more vectors or the invention, one or more host cells of the invention, or any combination thereof.

As discussed in more detail herein above, IL-17A is involved in many diseases. Accordingly the polypeptide, fusion construct, construct, nucleic acid molecules, vectors, host cells of the invention or any combination thereof are useful as a medicament. It is preferred that within said pharmaceutical composition the polypeptide, fusion construct, construct, nucleic acid molecules, vectors, host cells of the invention or any combination thereof are the only active agent. The pharmaceutical composition is preferably administered to mammals such as domestic and pet animals. Most preferred it is administered to humans. The pharmaceutical compositions described herein will be administered to the subject at a suitable dose.

The pharmaceutical composition for use in accordance with the present invention can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. The pharmaceutical composition may, accordingly, be administered orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable excipients. Also diagnostic compositions of the invention may be manufactured in any conventional manner.

The pharmaceutical composition of the invention may be administered as the sole active ingredient or in conjunction with, e.g. as an adjuvant to or in combination with, other drugs, e.g. immunosuppressive or immune modulating agents or other anti-inflammatory agents, e.g. for the treatment or prevention of diseases mentioned above. For example, the polypeptides, fusion constructs and constructs of the invention may be used in combination with immunosuppressive monoclonal antibodies, e.g. monoclonal antibodies with affinity to leukocyte receptors, e.g. MHC, CD2, CD3, CD4, CD7, CD8, CD25, CD28, CD40, CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (e.g. designated ATCC 68629) or a mutant thereof, e.g. LEA29Y; adhesion molecule inhibitors, e.g. LFA-I antagonists, ICAM-1 or -3 antagonists, VCAM-4 antagonists or VLA-4 antagonists. In addition, the polypeptides, fusion constructs and constructs of the invention may be used in combination with DMARD (disease-modifying anti-rheumatic drugs), gold salts, sulphasalazine, anti-malarias, methotrexate, D-penicillamine, azathioprine, mycophenolic acid, cyclosporine A, tacrolimus, sirolimus, minocycline, leflunomide, glucocorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CCI779, ABT578, AP23573 or TAFA-93; an ascomycin having immuno-suppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; or a chemotherapeutic agent, e.g. paclitaxel, gemcitabine, cisplatinum, doxorubicin or 5-fluorouracil; (other) anti-TNFα agents, e.g. monoclonal antibodies to TNFα (preferably comprising SEQ ID NOs 11 and/or 12), e.g. infliximab, adalimumab, CDP870, or receptor constructs to TNF-RI or TNF-RII, e.g. Etanercept, PEG-TNF-RI; blockers of proinflammatory cytokines, IL-1 blockers, e.g. Anakinra or IL-1 trap, AAL160, ACZ 885, IL-6 blockers; inhibitors or activators of proteases, e.g. metalloproteases, anti-IL-15 antibodies, anti-IL-6 antibodies, anti-IL-23 antibodies, anti-IL-22 antibodies, anti-IL-21 antibodies, anti-IL-12 antibodies, anti-IFN-gamma antibodies, anti-IFN-alpha antibodies, anti-CD20 antibodies, anti IL-17 antibodies, anti-IgGE antibodies, NSAIDs, such as aspirin or an anti-infectious agent. Other suitable drugs may include an ACE inhibitor, a Renin inhibitor, an ADH inhibitor, an Aldosteron inhibitor, and an Angiotensin receptor blocker. Naturally, this list of agents for co-administration is not limiting nor complete.

In general terms, the pharmaceutical composition of the invention is used in the treatment or prevention of a IL-17A-mediated disease.

Pharmaceutical compositions of the invention preferably comprise a pharmaceutically acceptable carrier or excipient. By "pharmaceutically acceptable carrier or excipient" is meant a non-toxic solid, semisolid or liquid filler, diluent, encapsulating material or formulation auxiliary of any type. Examples of pharmaceutically acceptable carriers or excipients are described, e.g., in Ansel et al., "Pharmaceutical Dosage Forms and Drug Delivery Systems", 7th edition, Lippincott Williams & Wilkins Publishers, 1999.

The diagnostic composition of the invention is useful in the detection of an undesired physiological glycosylated IL17A level, in particular glycosylated IL17A of SEQ ID NO: 10, e.g. in different cells, tissues or another suitable sample. Said detection typically comprises contacting a sample with the polypeptide, fusion construct, construct, nucleic acid molecule, vector, host cell of the invention or any combination thereof, and detecting the presence of a glycosylated IL17A, in particular the glycosylated IL17A of SEQ ID NO: 10 in the sample. Accordingly, the diagnostic composition of the invention may be used for assessing the onset or the disease status and in particular a disease state which is further defined herein below.

In one embodiment of the present invention described herein above, the polypeptide of the invention is linked to are fluorescent dye, a photosentisizer, a radionuclide, or a contrast agent for medical imaging. Such fusion constructs are particularly suitable for diagnostic applications.

The diagnostic composition of the invention can be administered as sole active agent or can be administered in combination with other agents, if the diagnostic composition is, for example, used to identify sites of undesired physiological glycosylated IL17A levels within a subject. In general terms, the diagnostic composition of the invention is used in the diagnosis of a IL-17A-mediated disease.

The dosage of the diagnostic and pharmaceutical compositions of the invention, will, of course, vary depending upon the particular polypeptide, fusion construct, construct, one or more nucleic acid molecules, one or more vectors, one or more host cells of the invention or any combination thereof, the individual patient group or patient, the optional presence of further diagnostically or medically active compounds and the nature and severity of the disease to be diagnosed or treated. However, it is presently preferred that the diagnostic or pharmaceutical composition is used in dosages of about 0.01 mg to about 20 mg per kilogram body weight, preferably about 0.1 mg to about 5 mg per kilogram body weight. Diagnostic or pharmaceutical compositions may be administered more than once, e.g. to monitor the course of a disease in case of diagnostic composition or to prolong treatment in case of a pharmaceutical composition. Preferably, the frequency of administration of the diagnostic or pharmaceutical composition is in the range of daily up to about once every 3 months, preferably about once every 2 weeks up to about once every 10 weeks, more preferably once every 4 to 8 weeks. A preferred dosage regimen involves the administration of the diagnostic or pharmaceutical compositions of the invention once per month to once every 2 to 3 months or less frequently.

In a preferred embodiment of the invention, said pharmaceutical composition is for the use in a method of treatment of an inflammatory, autoimmune and/or bone loss-related disease.

In a more preferred embodiment of the invention, the disease is selected from the group consisting of arthritis, preferably rheumatoid arthritis, arthritis chronica progrediente, reactive arthritis, psoriatic arthritis, enterophathic arthritis and arthritis deformans, rheumatic diseases, spondyloarthropathies, ankylosing spondylitis, Reiter syndrome, hypersensitivity (including both airways hypersensitivity and dermal hypersensitivity), allergies, systemic lupus erythematosus, inflammatory muscle disorders, polychondritis, sclerodoma, Wegener granulomatosis, dermatomyositis, Steven-Johnson syndrome, chronic active hepatitis, myasthenia gravis, psoriasis, idiopathic sprue, autoimmune inflammatory bowel disease, ulcerative colitis, Crohn's disease, Irritable Bowel Syndrome, endocrine ophthalmopathy, Graves disease, sarcoidosis, multiple sclerosis, primary biliary cirrhosis, juvenile diabetes (diabetes mellitus type I), autoimmune haematological disorders, hemolytic anaemia, aplastic anaemia, pure red cell anaemia, idiopathic thrombocytopenia, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, tumors, inflammatory disease of skin, cornea inflammation, myositis, loosening of bone implants, metabolic disorders, atherosclerosis, diabetes, and dislipidemia, bone loss, osteoarthritis, osteoporosis, periodontal disease of obstructive or inflammatory airways diseases asthma, bronchitis, pneumoconiosis, pulmonary emphysema, acute and hyperacute inflammatory reactions, acute infections, septic shock, endotoxic shock, adult respiratory distress syndrome, meningitis, pneumonia, severe burns, cachexia wasting syndrome, stroke, herpetic stromal keratitis and dry eye disease.

All of the above-specified diseases have in common that their origin and/or symptom(s) are IL-17A- and/or Th-17-related.

The Figures show

FIG. 1 shows size exclusion chromatograms (SEC) of IL-17A-binding polypeptides of the invention: (A) 1 L3-B09 (SEQ ID NO: 3), (B) 11L0-C6 (SEQ ID NO: 4), (C) 11 L5-B06 (SEQ ID NO: 5), (D) 11L6-F03 (SEQ ID NO: 6), (E) 11L9-C09 (SEQ ID NO: 7), (F) 11L10-A05 (SEQ ID NO: 8), (G) 11L11-A09 (SEQ ID NO: 9).

FIG. 3 depicts the results of the dose-dependent in vitro inhibition of glycosylated and non-glycosylated IL-17A by Fyn SH3 derived binders described in WO2011/023685: (A) Fyn SH3 derived IL-17 binder 2C1 (SEQ ID NO: 107 described in WO2011/023685). (B) Fyn SH3 derived IL-17 binder A1_2 ("A1") (SEQ ID NO: 53 described in WO2011/023685). (C) Fyn SH3 derived IL-17 binder B1_2 ("B1") (SEQ ID NO: 39 described in WO2011/023685).

Figure 4:
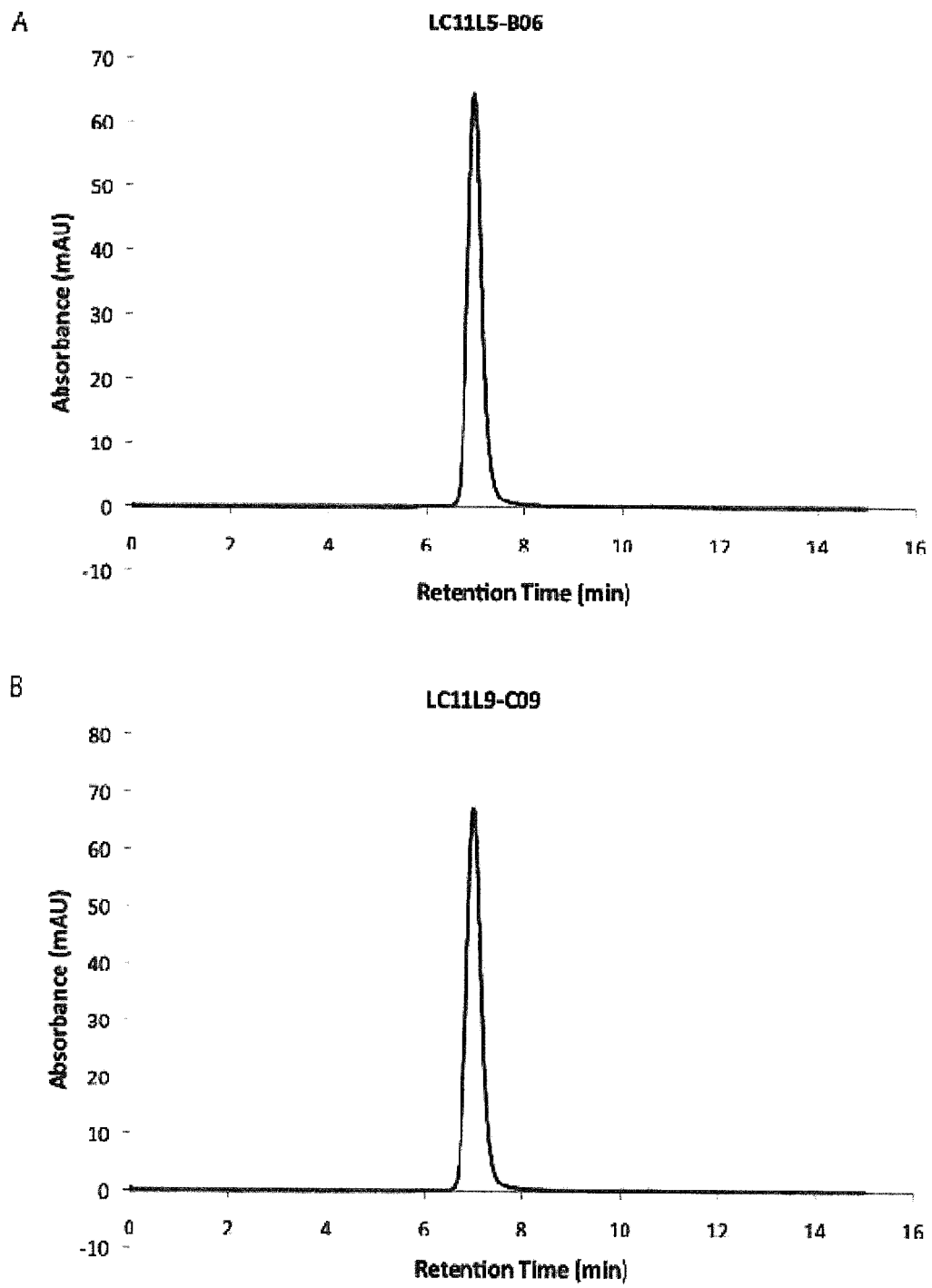

FIG. 4 shows the size exclusion chromatograms (SEC) of the bispecific IL-17A/TNFα binding polypeptides of the invention: (A) LC11L5-B06 (bispecific construct (according to the invention) with heavy chain and light chain consisting of the sequences of SEQ ID NOs: 12 and 16, respectively) and (B) LC11L9-C09 (bispecific construct (according to the invention) with heavy chain and light chain consisting of the sequences of SEQ ID NOs: 12 and 17, respectively).

FIG. 5 shows the simultaneous inhibition of IL-17A and TNFα by the bispecific anti-IL-17A/TNFα fusion proteins. Gro-alpha ELISA levels in the supernatants are shown after the stimulation of HT-29 cells with 200 pM TNFα and 400 pM IL-17A. After addition of the indicated concentrations of LC11L5-B06 (SEQ ID NOs: 12 (heavy chain) and 16 (light chain fusion)) (FIG. 5.A) or LC11L9-C09 (SEQ ID NOs: 12 (heavy chain) and 17 (light chain fusion)) (FIG. 5.B), a dose-dependent inhibition of IL-17A and TNFα can be observed because the Gro-alpha levels decline with higher concentrations of the inhibitors. As controls, cells were treated with the single cytokines (IL-17A or TNFα) or with medium only. Mean values of triplicates are shown, error bars represent standard deviations (SD).

Figure 6:
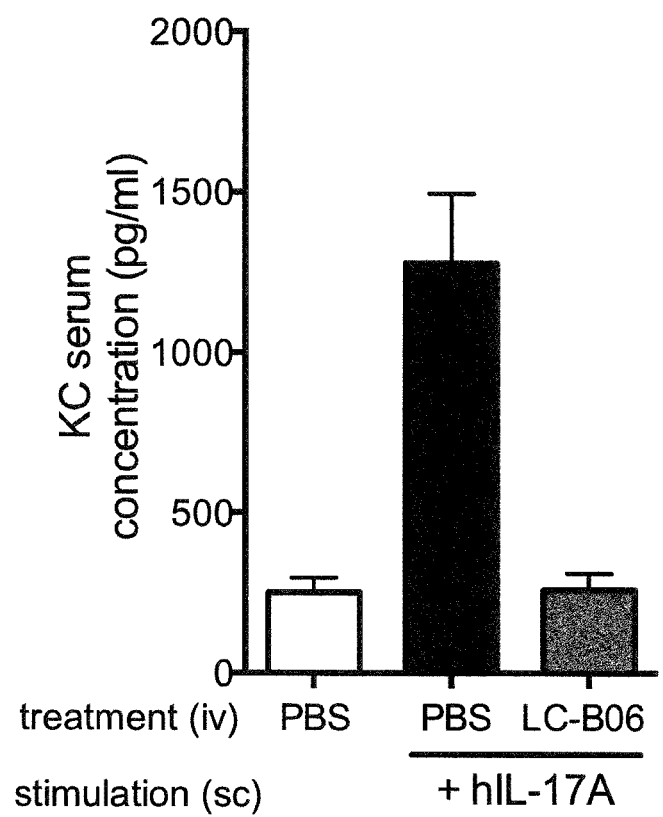

FIG. 6 depicts the inhibition of human IL-17A and TNFα in vivo. (A) and (B): Mice were injected intravenously (i.v.) with LC11L5-B06 (designated as "LC-B06") (SEQ ID NOs: 12 (heavy chain) and 16 (light chain fusion)), followed by s.c. injection of human IL-17A (hIL-17A) (A) or human TNFα (hTNFα) (B). Two hours after the administration of the indicated cytokine, blood samples were taken from the mice and KC levels were detected by ELISA. Mice that received either an intravenous injection of the anti-TNFα antibody (FIG. 6.B) ("aTNFαmAb") or PBS are shown as well. As a control, basal KC levels are shown (mice treated with PBS only (i.v.), without cytokine stimulation). (C) and (D): LC11L9-C09 (designated as "LC-C09") (SEQ ID NOs: 12 (heavy chain) and 17 (light chain fusion)) were injected intravenously (i.v.) in mice, followed by s.c. injection of IL-17A (C) or TNFα (D). Two hours after the administration of the indicated cytokine, blood samples were taken from the mice and KC levels were detected by ELISA. Mice that received either an intravenous injection of the anti-TNFα antibody (FIG. 6.D) ("aTNFαmAb") or PBS are shown as well. As a control, basal KC levels are shown (mice treated with PBS only (i.v.), without cytokine stimulation). Mean KC levels of 5 mice per group are shown (±SEM).

FIG. 7 shows the serum concentrations of (A) LC11L5-B06 (SEQ ID NOs: 12 (heavy chain) and 16 (light chain fusion)) and (B) LC11L9-C09 (SEQ ID NOs: 12 (heavy chain) and 17 (light chain fusion)) at different time-points after a single i.v. injection into C57BL/6 in mice. The concentration in serum was determined by ELISA using both TNFα and IL-17A as capturing agents (indicated in brackets). The last time-points (24 h-168 h) were used to calculate the terminal half-lives. Mean serum concentrations of 5 mice are plotted versus time, error bars represent standard deviations (SD).

FIG. 8 shows a sequence alignment of SEQ ID NOs: 3 to 9 and 20. SEQ ID NOs 3 to 9 correspond to the internal designations also in the examples of the application as it is evident from FIG. 8.

FIG. 9 depicts the results of the dose-dependent in vitro inhibition of glycosylated and non-glycosylated IL-17A by Fyn-SH3 derived polypeptide of the invention 11L11-A09 (SEQ ID NO: 9).

Figure 10:
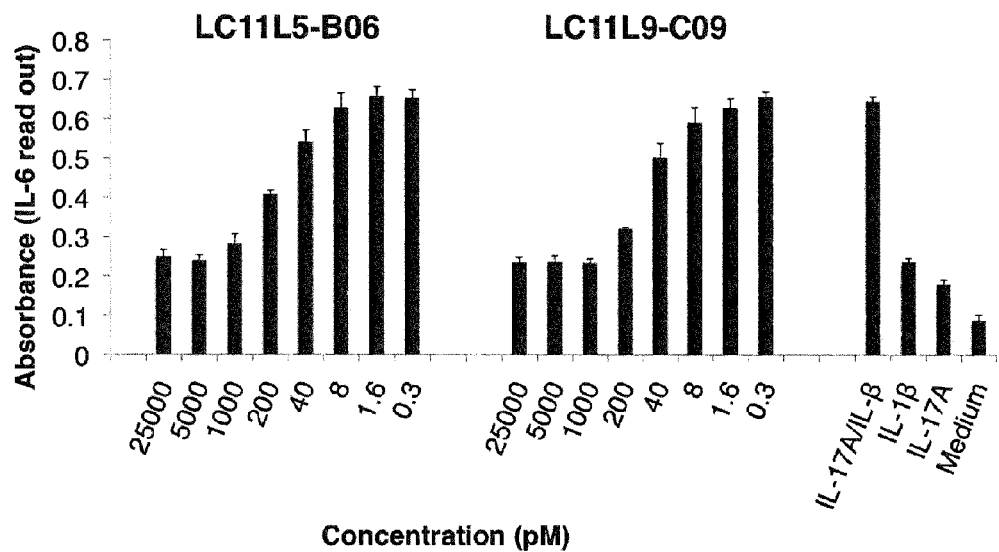

FIG. 10 shows the inhibition of IL-17A by the bispecific anti-IL-17A/TNFα fusion proteins LC11L5-B06 and LC11L9-C09. IL-6 ELISA levels in the cell culture supernatants are shown after the stimulation of NHDF cells with IL-17A and IL-1β ("IL-17A/IL-1β"). After addition of the indicated concentrations of LC11L5-B06 (SEQ ID NOs: 12 (heavy chain) and 16 (light chain fusion)) or LC11L9-C09 (SEQ ID NOs: 12 (heavy chain) and 17 (light chain fusion)), a dose-dependent inhibition of IL-17A mediated IL-6 release was observed. In control experiments, cells were treated with the single cytokines ("IL-17A" or "IL-1β") or with cell culture medium only ("Medium"). Mean values of triplicates are shown, error bars represent standard deviations (SD).

Figure 11:
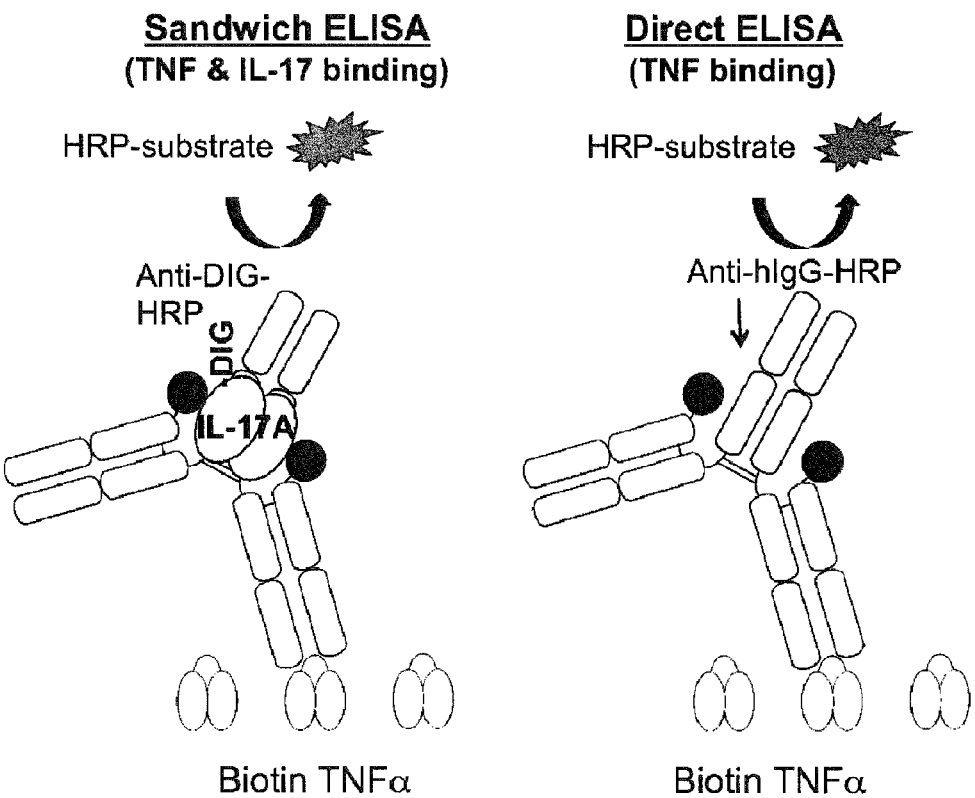

FIG. 11 shows the Sandwich ELISA and Direct ELISA methods. (left) Sandwich ELISA was performed to detect intact LC11L5-B06 and LC11L9-C09 molecules. Biotinylated TNF was immobilized in the wells of neutravidin-coated micro titer 96 well plates. Plasma containing LC11L5-B06 or LC11L9-C09 was added to the wells. For detection, digoxigenin-labeled IL-17A was used, followed by an anti-digoxigenin antibody-HRP conjugate for substrate processing and color development. (right) Direct ELISA was performed to detect specific TNF binding. Biotinylated TNF was immobilized in the wells of neutravidin-coated micro titer 96 well plates. Plasma containing LC11L5-B06 or LC11L9-C09 was added to the wells. Bound LC11L5-B06 or LC11L9-C09 was detected using an anti-human IgG antibody-HRP-conjugate for substrate processing and color development.

FIG. 12 shows the plasma concentrations of (A) LC11L5-B06 (SEQ ID NOs: 12 (heavy chain) and 16 (light chain fusion)) and (B) LC11L9-C09 (SEQ ID NOs: 12 (heavy chain) and 17 (light chain fusion)) at different time-points after a single i.v. injection into cynomolgus monkeys. The concentration in plasma was determined by Sandwich ELISA using TNFα as capturing agent and digoxigenin-labeled IL-17A followed by an anti-digoxigenin antibody-HRP conjugate for substrate processing and color development. Mean plasma concentrations of 3 cynomolgus monkeys are plotted versus time, error bars represent standard deviations (SD).

FIG. 13 shows the plasma concentrations of LC11L5-B06 (A) or LC11L9-C09 (B) in cynomolgus monkeys determined by Sandwich ELISA and Direct ELISA. The plasma concentrations are comparable for both proteins, indicating that LC11L5-B06 and LC11L9-C09 are stable in cynomolgus monkeys for at least 220 hours.

The Examples illustrate the invention.

EXAMPLE 1

Fyn SH3-Derived Polypeptides of the Invention Bind to IL-17A as Determined by Monoclonal Lysate ELISA Methods Using the Fynomer phage libraries described in Schlatter et al. (Schlatter et al. (2012) mAbs, 4(4) p. 497-50) Fyn-SH3 derived binding proteins specific to IL-17A were isolated using recombinant IL-17A (R&D Systems) as antigen and standard phage display as selection technology (Grabulovski D. et al., (2007) J Biol Chem 282, p. 3196-3204, Viti, F. et al. (2000) Methods Enzymol. 326, 480-505). Fyn SH3-derived polypeptide of the invention 1 L3-B09 (SEQ ID NO: 3) carrying the n-src-loop sequence "STHEYE" (SEQ ID NO: 2) was enriched during the selection process. 1L3-B09 (SEQ ID NO: 3) bound IL-17A (see Example 2) and was surprisingly found to inhibit glycosylated IL-17A as good as non-glycosylated IL-17A (see Example 3). In order to obtain Fyn SH3-derived IL-17A binders with higher affinities, 1L3-B09 (SEQ ID NO: 3) was used as template for affinity maturation. The n-src-loop sequence "STHEYE" (SEQ ID NO: 2) was kept constant and was combined with a randomized RT-loop repertoire (6 amino acid residues designated as $(X^1)(X^2)(X^3)(X^4)(X^5)(X^6)$ in SEQ ID NO: 1). The process of affinity maturation library generation was essentially the same as described for cloning of the naïve library with a randomized RT-loop ("library 0" in Schlatter et al. (2012) mAbs, 4(4) p. 497-50).

After naïve and affinity maturation selections, enriched Fyn SH3-derived polypeptides were screened for binding to IL-17A by lysate ELISA. DNA encoding the Fyn SH3-derived binding proteins were cloned into the bacterial expression vector pQE12 (Qiagen) so that the resulting constructs carried a C-terminal myc-hexahistidine tag as described in Grabulovski et al. (Grabulovski et al. (2007) JBC, 282, p.

3196-3204). The polypeptides were expressed in the cytosol of E. coli bacteria in a 96-well format and 200 µl of cleared lysate per well was prepared as described in Bertschinger et al. (Bertschinger et al. (2007) Protein Eng Des Sel 20(2): p. 57-68). Briefly, transformed bacterial colonies were picked from the agar plate and grown in a round bottom 96-well plate (Nunc, cat. no. 163320) in 200 µl 2×YT medium containing 100 µg/ml ampicillin and 0.1% (w/v) glucose. Protein expression was induced after growth for 3 h at 37° C. and 200 r.p.m. by adding 1 mM IPTG (Applichem, Germany). Proteins were expressed overnight in a rotary shaker (200 r.p.m., 30° C.). Subsequently, the 96-well plate was centrifuged at 1800 g for 10 min and the supernatant was discarded. The bacterial pellets were resuspended in 200 µl lysis buffer (50 mM $NaH_2PO_4$, 300 mM NaCl, 10 mM imidazole, pH 8.0) containing 1 mg/ml lysozyme and left for 30 min on ice. Afterwards, the bacterial cells were lysed by sonication in a water bath (six bursts for 10 s) and then centrifuged at 1800 g for 10 min. Monoclonal bacterial lysates were used for ELISA: biotinylated IL-17A (produced in-house in HEK EBNA cells, biotinylation was performed with NHS-PEO4-biotin (Pierce) according to the manufacturer's instructions) was immobilized on streptavidin-coated wells (StreptaWells, High Bind, Roche), and after blocking with PBS, 2% milk (Rapilait, Migros, Switzerland), 50 µl of PBS, 4% milk containing 6 µg/ml anti-myc antibody 9E10 (final concentration 3 µg/ml) and 50 µl of bacterial lysate were applied. After incubating for 1 h and washing, bound Fyn SH3-derived polypeptides were detected with anti-mouse-HRP antibody conjugate (Sigma). The detection of peroxidase activity was done by adding BM blue POD substrate (Roche) and the reaction was stopped by adding 1 M $H_2SO_4$. The DNA sequence of the specific binders was verified by DNA sequencing.

Results

The amino acid sequences of ELISA positive Fyn SH3-derived polypeptides binding to IL-17A is presented in SEQ ID NOs: 3 to 9 as appended in the sequence listing.

EXAMPLE 2

Fyn SH3-Derived Polypeptides of the Invention Bind to Glycosylated Human IL-17A with High Affinities This example shows the expression yields of Fyn SH3-derived IL-17A-binding polypeptides and the characterization of these polypeptides by size exclusion chromatography and surface plasmon resonance experiments.

Methods a) Expression Yields of Fyn SH3-Derived IL-17A-Binding Polypeptides

Fyn SH3-derived IL-17A-binding polypeptides were expressed in the cytosol of TG1 E. coli bacteria as well as purified as described in Grabulovski et al. (Grabulovski et al. (2007) JBC, 282, p. 3196-3204).

b) Size Exclusion Chromatography (SEC)

For the parental Fyn SH3-derived IL-17A binding polypeptide 1L3-B9 (SEQ ID NO: 3) Size Exclusion Chromatography (SEC) was performed on an AKTA FPLC system using a Superdex 75 Short Column (5/150) (GE Healthcare). SEC of the affinity matured clones 11L0-C06 (SEQ ID NO: 4), 11L5-B06 (SEQ ID NO: 5), 11L6-F03 (SEQ ID NO: 6), 11L9-C09 (SEQ ID NO: 7), 11L10-A05 (SEQ ID NO: 8) and 11L11-A09 (SEQ ID NO: 9) were performed on an Agilent Technologies 1200 Infinity Series HPLC instrument using a SEC-3 column (Agilent).

c) Affinity Measurements

Affinity measurements were performed using a BIAcore T200 instrument (GE Healthcare). For the interaction analysis between glycosylated IL-17A (produced in-house in HEK EBNA cells) and monomeric Fyn SH3-derived IL-17A-binding polypeptides, a Series S CM5 chip (GE Healthcare) was used with 2000 RU IL-17A immobilized using the Amine coupling kit (GE healthcare). The running buffer was PBS containing 0.05% Tween 20. The interactions were measured at a flow of 30 µl/min and injection of different concentrations of Fyn SH3-derived IL-17A-binding polypeptides. All kinetic data of the interaction were evaluated using BIAcore T200 evaluation software.

Results a) Expression Yields

The expression yields for monomeric Fyn SH3-derived IL-17A-binding polypeptides of the invention ranged from 14 to 57 mg/liter of bacterial culture under non-optimized conditions in shake flasks (Table 1).

TABLE 1

Expression yields of Fyn SH3-derived IL-17A-binding polypeptides produced in TG1 E. coli bacteria

| Fynomer | SEQ ID NO. | Yield (mg/l) |
|---|---|---|
| 1L3-B09 | 3 | 57 |
| 11L0-C06 | 4 | 43 |
| 11L5-B06 | 5 | 36 |
| 11L6-F03 | 6 | 14 |
| 11L9-C09 | 7 | 14 |
| 11L10-A05 | 8 | 32 |
| 11L11-A09 | 9 | 35 | b) Size Exclusion Chromatography (SEC)

Size exclusion chromatography (SEC) profiles demonstrated that all constructs eluted mainly as single, monomeric peaks (FIG. 1).

c) Affinity Measurements

The binding properties were analyzed by real-time interaction analysis on a BIAcore chip revealing the following dissociation constants ($K_D$) for selected IL-17A-binding polypeptides:

TABLE 2

Kinetics constants of the binding of Fyn SH3-derived IL-17A-binding polypeptides to recombinant human glycosylated IL-17A (produced in HEK EBNA cells).

| Fynomer | SEQ ID NO. | $K_D$ (nM) |
|---|---|---|
| 1L3-B09 | 3 | 245 |
| 11L0-C06 | 4 | 7 |
| 11L5-B06 | 5 | 12 |
| 11L6-F03 | 6 | 11 |
| 11L9-C09 | 7 | 11 |
| 11L10-A05 | 8 | 7 |
| 11L11-A09 | 9 | 24 |

EXAMPLE 3

Fyn SH3-Derived Polypeptides of the Invention Inhibit Glycosylated IL-17A

The parental clone 1 L3-B09 and five affinity matured Fyn SH3-derived polypeptides of the invention with the highest affinity to IL-17A (11L0-006 (SEQ ID NO: 4), 11L5-B06 (SEQ ID NO: 5), 11L6-F03 (SEQ ID NO: 6), 11L9-C09 (SEQ ID NO: 7), 11L10-A05 (SEQ ID NO: 8)) have been tested for their ability to inhibit IL-17A: IL-17A and TNFα induce the production of IL-6 in fibroblasts in a dose-dependent manner. The inhibitory activities of the indicated Fyn SH3-derived IL-17A-binding polypeptides were tested by stimulating human dermal fibroblasts with recombinant glycosylated IL-17A (produced in-house in HEK EBNA cells) and recombinant TNFα (Thermo Fisher Scientific) in the absence or presence of various concentrations of Fyn SH3-derived IL-17A binding polypeptides of the invention. Cell culture supernatants were taken after 24 h of stimulation and IL-6 concentration in the supernatant was determined by ELISA. The results show that the IL-17A binding polypeptides were able to specifically inhibit glycosylated IL-17A.

Methods

For endotoxin removal, the protein solutions were filtered three times with the Acrodisc Mustang E membrane (VWR). After filtration the endotoxin levels of the protein solutions containing inhibitory Fyn SH3-derived IL-17A-binding polypeptides of the invention were less than 0.1 EU/ml, as determined by the Limulus amebocyte lysate (LAL) test (PYROGENT Single test Gel Clot LAL Assay (Lonza)).

100 µl of a cell suspension containing about 3900 Normal Human Dermal Fibroblasts (PromoCell, NHDF-c, C12300) were distributed per well (96 well plate, TPP or Corning) and cultured for 24 hours at 37° C. (medium: Fibroblast Growth Medium C-23010, PromoCell). The supernatant was aspirated and after mixing different concentrations of Fyn SH3 derived IL-17A-binding polypeptides of the invention with IL-17A and TNFα containing medium (final concentrations 1 ng/ml and 50 pg/ml respectively), 100 µl of the corresponding solution was added per well. As controls PBS was mixed with the IL-17A/TNFα containing medium (pos. control="no inhibitor") and medium with the single cytokines IL-17A or TNFα only (latter being the "TNFα control" well). As a negative control PBS was mixed with medium only. For comparison, the assay has also been performed using non-glycosylated IL-17A (R&D Systems) using the same conditions. After 24 hours incubation at 37° C. the supernatant was in an ELISA to determine the IL-6 concentration using an IL-6 ELISA kit following the manufacturer's instructions (IL-6 ELISA kit, R&D Systems). The percentages of inhibition were plotted and $IC_{50}$ values were calculated using the software Prism 5.

The percentage of IL-17A inhibition was determined with the following formula:

$$\text{Inhibition}(\%) = 100 - \frac{((A450\text{-}650\text{ nm(sample)} - A450\text{-}650\text{ nm}(TNF\alpha\text{ control})) \times 100)}{(A450\text{-}650\text{ nm}(pos.\text{ control}) - A450\text{-}650\text{ nm}(TNF\alpha\text{ control}))}$$

Results

Figure 2:
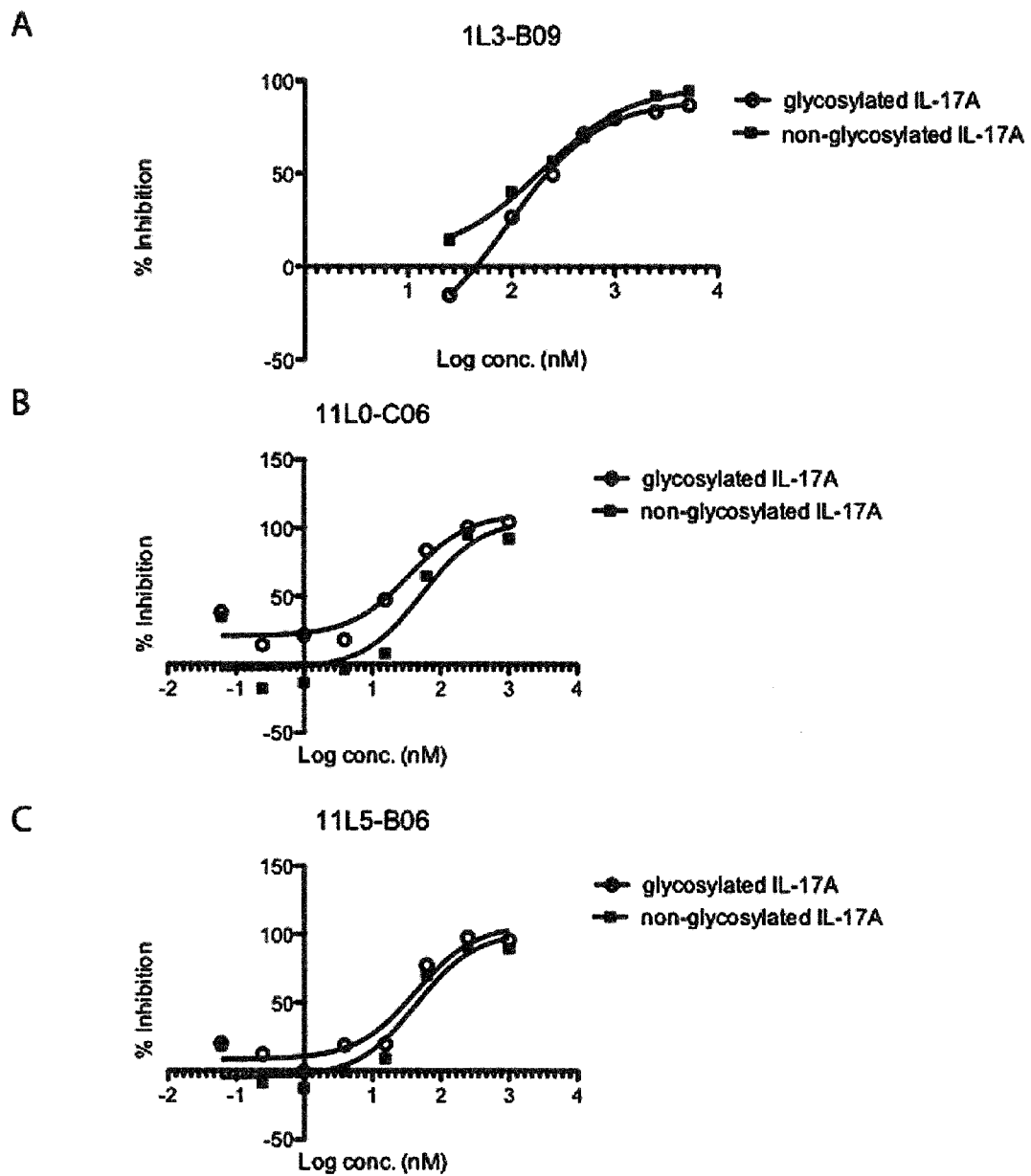
FIG. 2 depicts the results of the dose-dependent in vitro inhibition of glycosylated and non-glycosylated IL-17A by Fyn-SH3 derived polypeptides of the invention. A) 1 L3-B09 (SEQ ID NO: 3), (B) 11L0-C6 (SEQ ID NO: 4), (C) 11L5-B06 (SEQ ID NO: 5), (D) 11L6-F03 (SEQ ID NO: 6), (E) 11L9-C09 (SEQ ID NO: 7), (F) 11L10-A05 (SEQ ID NO: 8)

Normal Human Dermal Fibroblasts were incubated with IL-17A/TNFα and different concentrations of indicated Fyn SH3-derived IL-17A-binding polypeptides of the invention. It was observed that the Fyn SH3-derived polypeptides of the invention inhibited glycosylated IL-17A. The $IC_{50}$ values are shown in Table 3. FIG. 2 shows the dose-dependent inhibition curves of the indicated Fyn SH3-derived IL-17A-binding polypeptides of the invention inhibiting both glycosylated and non-glycosylated IL-17A. It was surprisingly found that the Fyn SH3-derived IL-17A-binding polypeptides described in this invention are able to completely inhibit glycosylated IL-17A with similar potencies as compared to non-glycosylated IL-17A. This is an advantageous property as compared to the Fyn SH3-derived IL-17A-binding polypeptides that were previously invented (WO2011/023685). FIG. 3 shows three examples of Fyn SH3-derived IL-17A-binding polypeptides described in WO2011/023685 (Fyn SH3 derived IL-17 binder 2C1 (SEQ ID NO: 107 described in WO2011/023685), Fyn SH3 derived IL-17 binder A1_2 (SEQ ID NO: 53 described in WO2011/023685) and Fyn SH3 derived IL-17 binder B1_2 ("B1") (SEQ ID NO: 39 described in WO2011/023685) that either do not inhibit glycosylated IL-17A completely even at high concentrations and/or show large differences in inhibition potency ($IC_{50}$ values) between glycosylated and non-glycosylated IL-17A (see FIG. 3).

TABLE 3

$IC_{50}$ values for inhibition of glycosylated IL-17A obtained for the Fyn SH3-derived IL-17A-binding polypeptides.

| Fynomer | SEQ ID NO. | $IC_{50}$ value (nM) |
|---|---|---|
| 1L3-B09 (parental clone) | 3 | 300 |
| 11L0-C06 | 4 | 35 |
| 11L5-B06 | 5 | 43 |
| 11L6-F03 | 6 | 63 |
| 11L9-C09 | 7 | 32 |
| 11L10-A05 | 8 | 28 |

EXAMPLE 4

Expression and Purification Yields of Bispecific Anti-IL-17A/TNFα Antibody-Fyn SH3 Derived IL-17A-Binding Polypeptide Fusions Fyn SH3-derived IL-17A-binding polypeptides (11L5-B06 (SEQ ID NO: 5) and 11L9-C09 (SEQ ID NO: 7)) have been genetically fused to the C-terminus of the light chain of an anti-TNFα antibody (SEQ ID NO: 11) via a 15 amino acid linker (linker: SEQ ID NO: 15). The resulting bispecific anti-IL-17A/TNFα constructs termed LC11L5-B06 (bispecific construct (according to the invention) with heavy chain and light chain consisting of the sequences of SEQ ID NOs: 12 and 16, respectively) and LC11L9-C09 (bispecific construct (according to the invention) with heavy chain and light chain consisting of the sequences of SEQ ID NOs: 12 and 17, respectively) were transiently transfected into FreeStyle CHO-S cells and expressed in serum-free/animal component-free media for 6-10 days. The proteins were purified from the supernatants by Protein A affinity chromatography (Mab Select Sure column; GE Healthcare) and by size exclusion chromatography (SEC; Superdex G200, 30/100 GL column; GE Healthcare) on an Äkta Purifier instrument (GE Healthcare). Concentrations were determined by absorbance measurements at 280 nm. Yields are listed in Table 4.

TABLE 4

Purification yields of bispecific antibody-Fyn SH3 derived IL-17A-binding polypeptides fusions produced in transiently transfected CHO-S cells.

| | SEQ ID NOs (heavy chain, light chain) | Yield (mg/l) |
|---|---|---|
| LC11L5-B06 | 12, 16 | 110 |
| LC11L9-C09 | 12, 17 | 110 |

After purification size exclusion chromatography has been performed using an ÄKTA FPLC system and a Superdex G200, 30/100 GL column (GE Healthcare). Size exclusion chromatography (SEC) profiles after purification demonstrated that both fusion proteins eluted as single, monomeric peaks showing that the fusion proteins have excellent biophysical properties (FIG. 4).

EXAMPLE 5

Affinity Measurements of Antibody-Fyn SH3 Derived IL-17A-Binding Polypeptides Fusions to Human and Cynomolgus IL-17A and TNFα

The affinities of LC11L5-B06 and LC11L9-C09 to IL-17A (human and Cynomolgus) and to TNFα (human and Cynomolgus) were measured using a BIAcore T200 instrument (GE Healthcare). A Series S CM5 chip (GE Healthcare) was coated with 8000 RU goat anti-human IgG Fc-specific antibody (Jackson Immunoresearch). The running buffer was PBS containing 0.05% Tween 20. The interactions were measured by capturing about 400 to 500 RU LC11L5-B06 or LC11L9-C09 at a flow rate of 30 µl/min, followed by injection of different concentrations of the antigens at a flow rate of 30 µl/min. All kinetic data of the interaction were evaluated using BIAcore T200 evaluation software. The affinities and are listed in Table 5 for the human antigens and in Table 6 for the Cynomolgus antigens.

TABLE 5

Dissociation constants of the binding of antibody-Fyn SH3 derived IL-17A-binding polypeptides fusions to recombinant human glycosylated IL-17A, and human TNFα.

| | SEQ ID NOs (heavy chain, light chain) | $K_D$ values for glycosylated human IL-17A (pM) | $K_D$ values for human TNFα (pM) |
|---|---|---|---|
| LC11L5-B06 | 12, 16 | 44 | 144 |
| LC11L9-C09 | 12, 17 | 48 | 89 |

TABLE 6

Dissociation constants of the binding of antibody-Fyn SH3 derived IL-17A-binding polypeptides fusions to recombinant Cynomolgus glycosylated IL-17A, and Cynomolgus TNFα.

| | SEQ ID NOs (heavy chain, light chain) | $K_D$ values for glycosylated Cynomolgus IL-17A (pM) | $K_D$ values for glycosylated Cynomolgus TNFα (pM) |
|---|---|---|---|
| LC11L5-B06 | 12, 16 | 63 | 120 |
| LC11L9-C09 | 12, 17 | 70 | 133 |

EXAMPLE 6

LC11L5-B06 and LC11L9-C09 Inhibit IL-17A and TNFα Simultaneously

IL-17A and TNFα induce the production of Gro-α in HT-29 cells (human colorectal adenocarcinoma cell line) in a dose-dependent manner. The inhibitory activities of the indicated constructs (LC11L5-B06 and LC11L9-C09) were tested by stimulating HT-29 cells (human colorectal adenocarcinoma cell line) with glycosylated IL-17A and TNFα in the absence or presence of various concentrations of LC11L5-B06 and LC11L9-C09. Cell culture supernatants were taken after 48 h of stimulation and assayed for Gro-α with ELISA.

Methods

LC11L5-B06 or LC11L9-C09 were diluted into assay medium (McCoy's 5A medium (GIBCO) supplemented with 10% FBS). 50 µl of each indicated concentration were mixed with 50 µl assay medium containing IL-17A (produced in-house in HEK EBNA cells) and TNFα (Thermo Fisher Scientific) at the final concentrations of 400 pM and 200 pM respectively. As a control, medium without inhibitor was prepared. Moreover, medium with the single cytokines only or without cytokines was prepared. After 1 hour incubation, 100 µl of a cell suspension containing about 20,000 HT-29 cells (ATCC, #HTB-38) were added to the solutions and distributed per well (96 well plate, TPP or Corning) and cultured for 48 hours at 37° C. and 5% $CO_2$. After 48 hours incubation at 37° C. the supernatant was removed and the Gro-α concentration was determined by ELISA according to the manufacturer's instructions (Gro-α ELISA kit, R&D Systems).

Results

FIG. 5 shows the Gro-alpha concentration (depicted as the ELISA signal) in the supernatant of HT-29 cells after stimulation with IL-17A, TNFα and a combination thereof. As shown in FIG. 5, the bispecific constructs LC11L5-B06 and LC11L9-C09 were able to inhibit in a dose-dependent manner simultaneously IL-17A and TNFα. The obtained apparent $IC_{50}$ values (Table 7) demonstrate that the bispecific compounds of the invention are able to inhibit IL-17A and TNFα with high potency.

TABLE 7

Apparent $IC_{50}$ values for simultaneous inhibition of IL-17A and TNFα obtained for bispecific antibody-Fyn SH3 derived IL-17A-binding polypeptides fusions.

| | SEQ ID NOs (heavy chain, light chain) | Apparent $IC_{50}$ value (pM) for simultaneous inhibition of IL-17A and TNFα |
|---|---|---|
| LC11L5-B06 | 12, 16 | 247 |
| LC11L9-C09 | 12, 17 | 222 |

EXAMPLE 7

LC11L5-B06 and LC11L9-C09 Inhibit IL-17A and TNFα In Vivo

The ability of LC11L5-B06 and LC11L9-C09 to inhibit IL-17A and TNFα in vivo was determined using an acute inflammation model in C57BL/6 mice. Human IL-17A binds and stimulates the mouse IL-17 receptor. When injected into mice, IL-17A triggers a massive increase of chemokine KC (CXCL1), which is detectable within 1-4 hours in the serum and lavage fluids of injected mice. Similar observations can be made for human TNFα, which also leads to a significant increase in KC-serum levels when injected into mice.

Methods

Mice (C57BL/6, Charles River) were intravenously injected with the inhibitors LC11L5-B06 (2 mg/kg), LC11L9-C09 (2 mg/kg) or as control for TNF inhibition a commercially available anti-TNFα antibody (2 mg/kg) (adalimumab (HUMIRA®)) diluted in endotoxin-free PBS (5 mice per group). 3.5 hours after intravenous injection of the inhibitors, KC expression was stimulated with human IL-17A or human TNFα by subcutaneous administration (3 µg IL-17A per mouse or 0.25 µg TNFα per mouse). Two hours later, blood was withdrawn for serum sampling and KC concentration was determined using a commercially available KC ELISA kit following the manufacturer's instructions (Quantikine mouse KC immunoassay, R&D Systems).
Results After s.c. injection of human IL-17A or TNFα into mice the animals overexpress a chemokine called KC. Elevated KC levels in the sera of mice can be measured by ELISA. Previous i.v. injection of the Fyn SH3-derived polypeptide fusions of the invention (LC11L5-B06 and LC11L9-C09) and the control anti-TNFα antibody (FIGS. 6.B and 6.D) prevented the up-regulation of KC in vivo. FIG. 6 shows the potent inhibition properties of LC11L5-B06 (designated as "LC-B06") and LC11L9-C09 (designated as "LC-C09").

EXAMPLE 8

LC11L5-B06 and LC11L9-C09 Exhibit an Antibody-Like PK Profile In Vivo

The in vivo pharmacokinetic properties of the fusion proteins of the invention LC11L5-B06 and LC11L9-C09 were determined by measuring the concentrations by ELISA in mouse serum taken at different time points after a single i.v. injection.
Methods LC11L5-B06 and LC11L9-C09 were injected intravenously into 5 mice (C57BL/6, Charles River) at a dose of 10 mg/kg. After 10 minutes, 6, 24, 48, 96, 120, 144 and 168 hours about 20 µl of blood was taken from the vena saphena with the capillary Microvette CB 300 (Sarstedt). Blood samples were centrifuged for 10 min at 9500×g and the serum was stored at −20° until ELISA analysis was performed. Using dilution series with known concentrations LC11L5-B06 and LC11L9-C09, the concentration in serum was determined by ELISA using both TNFα and IL-17A as capturing agents: 50 µl of biotinylated IL-17A (120 nM) (R&D Systems, biotinylated using EZ-link NHS-PGE4-biotin (Pierce) according to the manufacturer's instructions) or 50 µl of biotinylated TNFα (10 nM) (Thermo Scientific, biotinylated using EZ-link NHS-PGE4-biotin (Pierce) according to the manufacturer's instructions) were added to streptavidin-coated wells (Reactibind, Pierce) and after blocking with 200 µl PBS, 4% milk (Rapilait, Migros, Switzerland), 50 µl of diluted serum samples (in PBS, 4% milk) was added. After incubation for 1 h and washing with PBS, bound antibody Fynomer fusion proteins were detected with protein A-HRP conjugate (Sigma). Peroxidase activity was detected by addition of QuantaRed enhanced chemifluorescent HRP substrate (Pierce). Fluorescence intensity was measured after 1 to 5 min at 544 nm (excitation) and 590 nm (emission). From the concentrations of LC11L5-B06 and LC11L9-C09 determined in serum at different time points and the resulting slope k of the elimination phase (plotted in a semi-logarithmic scale), the half-lives were calculated using to the formula $t_{1/2}=\ln 2/-k$.
Results The serum concentrations of LC11L5-B06 and LC11L9-C09 are shown in FIG. 7. The half-lives determined from the elimination phase (beta phase, time-points 24 h-168 h) ranged between 4.9 days and 9.6 days for both fusion proteins (see Table 8), which is in the same range as reported half-life values for standard antibody therapeutics injected in mice. These data demonstrate that LC11L5-B06 and LC11L9-C09 have IgG-like in vivo PK properties.

TABLE 8

Terminal half-live values for the bispecific antibody-Fyn SH3 derived IL-17A-binding polypeptides fusions.

| | SEQ ID NOs (heavy chain, light chain) | Half-life (days) |
|---|---|---|
| LC11L5-B06 (IL-17A detection) | 12, 16 | 6.2 |
| LC11L5-B06 (TNFα detection) | 12, 16 | 9.6 |
| LC11L9-C09 (IL-17A detection) | 12, 17 | 4.9 |
| LC11L9-C09 (TNFα detection) | 12, 17 | 9.6 |

EXAMPLE 9

Fyn-SH3 Derived Polypeptide of the Invention 11L11-A09 Inhibits Glycosylated IL-17A Fynomer 11L11-A09 (SEQ ID NO: 9) has been tested for its ability to inhibit IL-17A.
Methods The experimental conditions were the same as described in Example 3 for the other Fyn SH3-derived polypeptides of the invention (SEQ ID NOs: 3-8).
Results Normal Human Dermal Fibroblasts were incubated with IL-17A/TNFα and different concentrations of the Fyn-SH3 derived polypeptide of the invention 11L11-A09 (SEQ ID NO: 9). It was observed that 11L11-A09 (SEQ ID NO: 9) inhibited glycosylated IL-17A with an $IC_{50}$ value of 66 nM (Table 9). FIG. 9 shows the dose-dependent inhibition curves of the Fyn-SH3 derived polypeptide of the invention 11L11-A09 (SEQ ID NO: 9), inhibiting both glycosylated and non-glycosylated IL-17A with a comparable potency and efficacy.

TABLE 9

$IC_{50}$ value for inhibition of glycosylated IL-17A obtained for the Fyn SH3-derived IL-17A-binding polypeptide 11L11-A09 (SEQ ID NO: 9).

| Fynomer | SEQ ID NO. | $IC_{50}$ value (nM) |
|---|---|---|
| 11L11-A09 | 9 | 66 |

EXAMPLE 10

LC11L5-B06 and LC11L9-C09 Inhibit Glycosylated IL-17A with High Potency

This example further demonstrates the ability of Fyn SH3-derived polypeptides of the invention to inhibit specifically glycosylated IL-17A. Bispecific anti-IL-17A/TNFα constructs LC11L5-B06 (bispecific construct (according to the invention) with heavy chain and light chain consisting of the sequences of SEQ ID NOs: 12 and 16, respectively) and LC11L9-C09 (bispecific construct (according to the invention) with heavy chain and light chain consisting of the sequences of SEQ ID NOs: 12 and 17, respectively) were expressed and purified as described in Example 4. The inhibitory activities of LC11L5-B06 and LC11L9-C09 were tested by stimulating normal human dermal fibroblasts (NHDF cells) with recombinant glycosylated IL-17A (produced in-house in HEK EBNA cells) and recombinant IL-1β (R&D Systems) to produce IL-6 in the absence or presence of various concentrations of LC11L5-B06 or LC11L9-C09. Cell culture supernatants were removed after 16-24 h of stimulation and IL-6 concentration in the supernatant was determined by ELISA. The results show that fusion proteins comprising the IL-17A binding polypeptides of the invention were able to specifically inhibit glycosylated IL-17A.

Methods

100 µl of a cell suspension containing about 3900 Normal Human Dermal Fibroblasts (PromoCell, NHDF-c, C12300) were distributed per well (96 well plate, TPP) and cultured for 24 hours at 37° C./5% $CO_2$ (medium: Fibroblast Growth Medium C-23010, PromoCell). The supernatant was aspirated and after mixing different concentrations of LC11L5-B06 or LC11L9-C09 (final concentrations shown in FIG. 10) with IL-17A and IL-1β containing medium (final concentrations: IL-17A: 64 pM; IL-1β: 10 fM), 100 µl of the corresponding solution was added to the cells (triplicates). In control experiments, PBS was mixed with the IL-17A/IL-1β containing medium ("IL-17A/IL-1β") and medium with the single cytokines "IL-17A" or "IL-1β" only (latter being the "IL-17A" and "IL-1β" control wells). As a negative control, PBS was mixed with medium only ("Medium"). After 16-24 hours of incubation at 37° C./5% $CO_2$ the IL-6 concentration in the supernatant was determined using an IL-6 ELISA kit following the manufacturer's instructions (IL-6 ELISA kit, R&D Systems). For the calculation of the $IC_{50}$ values, the percentages of inhibition were determined and $IC_{50}$ values were calculated using the software Prism 5.

The percentage of IL-17A inhibition was determined with the following formula:

$$\text{Inhibition}(\%) = 100 - \frac{((A450\text{-}650 \text{ nm(sample)} - A450\text{-}650 \text{ nm}(IL\text{-}1\beta)) \times 100)}{(A450\text{-}650 \text{ nm}(IL\text{-}17A/IL\text{-}1\beta) - A450\text{-}650 \text{ nm}(IL\text{-}1\beta))}$$

Results

FIG. 10 shows the ELISA values (absorbance) obtained for the determination of IL-6 concentrations in the supernatants of NHDF cells. As shown in FIG. 10, the bispecific constructs LC11L5-B06 and LC11L9-C09 were able to inhibit the IL-17A mediated IL-6 production in a dose-dependent manner, demonstrating that they were able to inhibit specifically glycosylated IL-17A. As expected, IL-1β induced IL-6 release could not be inhibited. The obtained $IC_{50}$ values for IL-17A inhibition (Table 10) show that the bispecific compounds of the invention are able to inhibit IL-17A with high potency.

TABLE 10

$IC_{50}$ values for inhibition of IL-17A obtained for bispecific antibody-Fyn SH3 derived IL-17A binding polypeptide fusions.

| | SEQ ID NOs (heavy chain, light chain) | $IC_{50}$ value (pM) for inhibition of IL-17A |
|---|---|---|
| LC11L5-B06 | 12, 16 | 121 |
| LC11L9-C09 | 12, 17 | 66 |

EXAMPLE 11

LC11L5-B06 and LC11L9-C09 are Stable In Vivo and Exhibit a Long Half-Life in Cynomolgus Monkey The pharmacokinetic properties of the fusion proteins of the invention LC11L5-B06 and LC11L9-C09 were determined by measuring their concentrations in cynomolgus monkey at different time points after a single i.v. injection. Using dilution series with known concentrations of LC11L5-B06 and LC11L9-C09, the concentration in plasma was determined using a "Sandwich ELISA", ensuring the measurement of only fully functional and intact bispecific molecules LC11L5-B06 and LC11L9-C09. To further demonstrate that LC11L5-B06 and LC11 L9-C09 stay intact and the Fyn SH3-derived polypeptides of the invention are not cleaved from the antibody in vivo (in cynomolgus monkeys) an additional ELISA was developed, which detects only the antibody component of the fusion proteins ("Direct ELISA"). The two ELISA detection methods are illustrated in FIG. 11.

Methods

Bispecific anti-IL-17A/TNFα constructs LC11L5-B06 (bispecific construct (according to the invention) with heavy chain and light chain consisting of the sequences of SEQ ID NOs: 12 and 16, respectively) and LC11L9-C09 (bispecific construct (according to the invention) with heavy chain and light chain consisting of the sequences of SEQ ID NOs: 12 and 17, respectively) were expressed and purified as described in Example 4. LC11L5-B06 and LC11L9-C09 were injected intravenously into 3 male cynomolgus monkeys at a dose of 3 mg/kg. Blood was taken from peripheral veins at the indicated time-points after end of dosing (0.6 ml of collection volume per sample). EDTA solution (7.5%) was used as anticoagulant. After blood collection, the samples were centrifuged at 4° C. for 10 min at 1200 g, and plasma was stored at −80° C. until analysis by ELISA.

"Sandwich ELISA":

Neutravidin-coated wells (Biomat MCP44-11) were blocked with 150 µl/well of Blocking Buffer (1×PBS-5% BSA) for 60 minutes at room temperature (RT) under gentle roto-orbital shaking set at 300 rpm. The wells were washed with 200 µl/well of Wash Buffer (1×PBS-0.1% Tween 20) and then incubated with 100 µl/well of a solution containing 0.2 µg/ml of biotinylated TNF-alpha (PeproTech, biotinylated using a biotin labeling kit from ANP Technologies according to the manufacturer's instructions) diluted in Assay Buffer (1×PBS-1% BSA) for 60 minutes at RT under gentle shaking. After three washes with 200 µl/well of Wash Buffer, samples, diluted 1:4 in Assay Buffer were dispensed to the wells (100 µl/well) and incubated for 1 hour under gentle shaking. The plate was washed 3 times (200 µl/well) with Wash Buffer prior to the addition of 100 µl/well of a solution containing 64 ng/ml of digoxigenylated IL-17A (PrepoTech, labeled with digoxigenin using a Digoxigenin Labeling Kit, purchased from Solulink, by following the supplier's recommended protocol) diluted in Assay Buffer. A further incubation for 1 hour at RT, under gentle shaking, was then carried out. After 3 washes (200 µl/well) with Wash Buffer the plate was incubated with 100 µl/well of the Anti-digoxigenin HRP-conjugated antibody (Roche), diluted 1:10000 in Assay Buffer. Incubation was carried out at room temperature for 60 minutes at 300 rpm. The plate was washed 3 times (200 µl/well) with Wash Buffer and 100 µl/well of TMB (Sigma) were immediately added and incubated for 5-10 minutes at room temperature in the dark. An aliquot (100 µl/well) of Stop Solution was finally added to each well to stop the enzymatic reaction. Optical density was measured at 450 nm using a Victor²V (Wallac Perkin Elmer) microtiter plate reader.

"Direct ELISA":

Neutravidin-coated 96 wells (Biomat MCP44-11) were blocked with 150 µl/well of Blocking Buffer (1×PBS-5% BSA) for 60 minutes at RT under gentle roto-orbital shaking set at 300 rpm. Wells were washed with 200 µl/well of Wash Buffer (1×PBS-0.1% Tween20) and then incubated with 100 µl/well of a solution of 0.2 µg/ml of biotinylated TNF-alpha diluted in Assay Buffer (1×PBS-1% BSA) for 60 minutes at RT under gentle shaking. After three washes with 200 µl/well of Wash Buffer, samples, diluted 1:4 in Assay Buffer, were dispensed to the wells (100 µl/well) and incubated for 1 hour under gentle shaking. The plate was washed 3 times (200 µl/well) with Wash Buffer prior to the addition of 100 µl/well of a solution of 44 ng/mL of HRP-conjugated anti-Human IgG monkey-adsorbed antibody (ABCam) diluted in Assay Buffer. A further incubation for 1 hour at RT, under gentle shaking, was then carried out. The plate was washed 3 times (200 µl/well) with Wash Buffer and 100 µl/well of TMB (Sigma) were immediately added and incubated for 5-10 minutes at room temperature in the dark. An aliquot (100 µl/well) of Stop Solution was finally added to each well to stop the enzymatic reaction. Optical density was measured at 450 nm using a Victor²V (Wallac Perkin Elmer) microtiter plate reader.

Pharmacokinetic analyses for LC11L5-B06 and LC11L9-C09 were performed with the plasma concentrations determined by the ELISA methods using the Watson package (v. 7.4, Thermo Fisher Scientific, Waltham, Mass., USA).

Results

Plasma concentrations of LC11L5-B06 and LC11L9-C09 are shown in FIG. 12. Both compounds exhibited a low clearance from the blood and a terminal half-life of several days in cynomolgus monkeys, as typically reported for standard monoclonal antibody therapeutics. Importantly, the plasma concentrations obtained using the two different ELISA methods are very similar, proving that LC11L5-B06 and LC11L9-C09 are stable in vivo for at least 220 hours and that the Fyn SH3 derived polypeptides are not cleaved from the antibody in cynomolgus monkeys (FIG. 13).

The invention claimed is:

1. A polypeptide that inhibits the activity of glycosylated IL-17A comprising:
(a) a peptide consisting of the amino acid sequence of (SEQ ID NO: 1)
GVTLFVALYDY($X^1$) ($X^2$) ($X^3$) ($X^4$) ($X^5$) ($X^6$)DLSFHKGEKFQIL
STHEYEDWWEARSLTTGETGYIPSNYVAPVDSIQ, wherein amino acid positions ($X^1$) to ($X^6$) may be any amino acid sequence; or
(b) a peptide that is at least 85% identical to the peptide of the amino acid sequence of (a),
wherein the identity determination excludes amino acid positions ($X^1$) to ($X^6$) and provided that the amino acid sequence STHEYE (SEQ ID NO: 2) in amino acid positions 31 to 36 of SEQ ID NO: 1 is conserved.

2. The polypeptide of claim 1, wherein
($X^1$) is A, K, S, D or E;
($X^2$) is N, Q, A, K, S or R;
($X^3$) is H, K, R, L or V;
($X^4$) is G or S;
($X^5$) is H, Q, A, W, V or N; and
($X^6$) is R, L or S.

3. The polypeptide of claim 1, wherein the polypeptide comprises a peptide consisting of the amino acid sequence of any one of SEQ ID NOs 3, 4, 5, 6, 7, 8, or 9.

4. A fusion construct comprising a polypeptide of claim 1 fused to a further compound.

5. The fusion construct of claim 4, wherein the further compound is a pharmaceutically active compound, a prodrug, a pharmaceutically-acceptable carrier, a diagnostically active compound, a cell penetrating enhancer, a compound modulating serum half-life, or a combination thereof.

6. The fusion construct of claim 4, wherein the further compound is
(a) a fluorescent dye,
(b) a photosentisizer,
(c) a radionuclide,
(d) a contrast agent for medical imaging,
(e) a cytokine,
(f) a toxic compound,
(g) a chemokine,
(h) a pro-coagulant factor,
(i) an enzyme for pro-drug activation,
(k) an albumin binder,
(l) an albumin,
(m) an IgG binder, or
(n) polyethylene glycol.

7. The fusion construct of claim 4, wherein the further compound is an antibody light chain, an antibody heavy chain, an $F_c$ domain of an antibody, an antibody, or a combination thereof.

8. The fusion construct of claim 7, wherein the further compound is located at the N-terminus of the polypeptide.

9. The fusion construct of claim 7, wherein the further compound comprises an antibody light chain comprising the amino acid sequence of SEQ ID NO: 11.

10. A construct comprising at least one copy of a fusion construct of claim 9 and at least one copy of the antibody heavy chain of SEQ ID NO: 12.

11. The construct of claim 10, wherein the construct comprises at least one copy of a fusion construct comprising the amino acid sequence of SEQ ID NO: 16 or 17 and at least one copy of the antibody heavy chain of the amino acid sequence of SEQ ID NO: 12.

12. A nucleic acid molecule encoding a polypeptide of claim 1.

13. A method of treating an inflammatory disease comprising administering a pharmaceutical composition comprising a polypeptide of claim 1, wherein the disease is psoriatic arthritis, psoriasis, rheumatoid arthritis, or autoimmune inflammatory bowel disease.

14. The fusion construct of claim 7, wherein the further compound comprises an antibody that specifically binds to TNFα.

15. A construct comprising two copies of a fusion construct of claim 9 and two copies of the antibody heavy chain of the amino acid sequence of SEQ ID NO: 12.

16. The construct of claim 10, wherein the construct comprises at least one copy of a fusion construct comprising the amino acid sequence of SEQ ID NO: 17 and at least one copy of the antibody heavy chain comprising the amino acid sequence of SEQ ID NO: 12.

17. The construct of claim 11, wherein the construct comprises two copies of a fusion construct comprising the amino acid sequence of SEQ ID NO: 16 and two copies of the antibody heavy chain comprising the amino acid sequence of SEQ ID NO: 12.

18. The construct of claim 16, wherein the construct comprises two copies of a fusion construct comprising the amino acid sequence of SEQ ID NO: 17 and two copies of the antibody heavy chain comprising the amino acid sequence of SEQ ID NO: 12.

* * * * *

SEQUENCE LISTING

```
<160> NUMBER OF SEQ ID NOS: 20

<210> SEQ ID NO 1
<211> LENGTH: 64
<212> TYPE: PRT
<213> ORGANISM: Artificial sequence
<220> FEATURE:
<223> OTHER INFORMATION: Polypeptide inhibits glycosylated IL 17A
      activity
<220> FEATURE:
<221> NAME/KEY: variant
<222> LOCATION: 12
<223> OTHER INFORMATION: Can be Cys, Asp, Glu, Phe, Gly, His, Ile, Lys,
      Leu, Met, Asn, Pro, Gln, Arg, Ser, Thr, Val, Trp, Tyr
<220> FEATURE:
<221> NAME/KEY: variant
<222> LOCATION: 13
<223> OTHER INFORMATION: Can be Cys, Asp, Glu, Phe, Gly, His, Ile, Lys,
      Leu, Met, Asn, Pro, Gln, Arg, Ser, Thr, Val, Trp, Tyr
<220> FEATURE:
<221> NAME/KEY: variant
<222> LOCATION: 14
<223> OTHER INFORMATION: Can be Cys, Asp, Glu, Phe, Gly, His, Ile, Lys,
      Leu, Met, Asn, Pro, Gln, Arg, Ser, Thr, Val, Trp, Tyr
<220> FEATURE:
<221> NAME/KEY: variant
<222> LOCATION: 15
<223> OTHER INFORMATION: Can be Cys, Asp, Glu, Phe, Gly, His, Ile, Lys,
      Leu, Met, Asn, Pro, Gln, Arg, Ser, Thr, Val, Trp, Tyr
<220> FEATURE:
<221> NAME/KEY: variant
<222> LOCATION: 16
<223> OTHER INFORMATION: Can be Cys, Asp, Glu, Phe, Gly, His, Ile, Lys,
      Leu, Met, Asn, Pro, Gln, Arg, Ser, Thr, Val, Trp, Tyr
<220> FEATURE:
<221> NAME/KEY: variant
<222> LOCATION: 17
<223> OTHER INFORMATION: Can be Cys, Asp, Glu, Phe, Gly, His, Ile, Lys,
      Leu, Met, Asn, Pro, Gln, Arg, Ser, Thr, Val, Trp, Tyr

<400> SEQUENCE: 1

Gly Val Thr Leu Phe Val Ala Leu Tyr Asp Tyr Ala Ala Ala Ala
1               5                   10                  15

Ala Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45
```

```
Thr Gly Tyr Ile Pro Ser Asn Tyr Val Ala Pro Val Asp Ser Ile Gln
    50                  55                  60

<210> SEQ ID NO 2
<211> LENGTH: 6
<212> TYPE: PRT
<213> ORGANISM: Artificial sequence
<220> FEATURE:
<223> OTHER INFORMATION: Recombinant src-loop

<400> SEQUENCE: 2

Ser Thr His Glu Tyr Glu
1               5

<210> SEQ ID NO 3
<211> LENGTH: 64
<212> TYPE: PRT
<213> ORGANISM: Artificial sequence
<220> FEATURE:
<223> OTHER INFORMATION: 1L3-B9

<400> SEQUENCE: 3

Gly Val Thr Leu Phe Val Ala Leu Tyr Asp Tyr Ala Asn His Gly Asn
1               5                   10                  15

Arg Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 4
<211> LENGTH: 64
<212> TYPE: PRT
<213> ORGANISM: Artificial sequence
<220> FEATURE:
<223> OTHER INFORMATION: 11L0-C6

<400> SEQUENCE: 4

Gly Val Thr Leu Phe Val Ala Leu Tyr Asp Tyr Lys Gln Lys Gly His
1               5                   10                  15

Leu Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 5
<211> LENGTH: 64
<212> TYPE: PRT
<213> ORGANISM: Artificial sequence
<220> FEATURE:
<223> OTHER INFORMATION: 11L5-B06

<400> SEQUENCE: 5

Gly Val Thr Leu Phe Val Ala Leu Tyr Asp Tyr Ser Ala Arg Gly Gln
1               5                   10                  15

Leu Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45
```

```
Thr Gly Tyr Ile Pro Ser Asn Tyr Val Ala Pro Val Asp Ser Ile Gln
    50                  55                  60
```

<210> SEQ ID NO 6
<211> LENGTH: 64
<212> TYPE: PRT
<213> ORGANISM: Artificial sequence
<220> FEATURE:
<223> OTHER INFORMATION: 11L6-F03

<400> SEQUENCE: 6

```
Gly Val Thr Leu Phe Val Ala Leu Tyr Asp Tyr Asp Lys Leu Ser Ala
1               5                   10                  15

Leu Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 7
<211> LENGTH: 64
<212> TYPE: PRT
<213> ORGANISM: Artificial sequence
<220> FEATURE:
<223> OTHER INFORMATION: 11L9-C09

<400> SEQUENCE: 7

```
Gly Val Thr Leu Phe Val Ala Leu Tyr Asp Tyr Glu Ser Val Ser Trp
1               5                   10                  15

Ser Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 8
<211> LENGTH: 64
<212> TYPE: PRT
<213> ORGANISM: Artificial sequence
<220> FEATURE:
<223> OTHER INFORMATION: 11L10-A05

<400> SEQUENCE: 8

```
Gly Val Thr Leu Phe Val Ala Leu Tyr Asp Tyr Ser Ser Arg Gly Val
1               5                   10                  15

Leu Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 9
<211> LENGTH: 64
<212> TYPE: PRT
<213> ORGANISM: Artificial sequence
<220> FEATURE:
<223> OTHER INFORMATION: 11L11-A09

<400> SEQUENCE: 9

-continued

```
Gly Val Thr Leu Phe Val Ala Leu Tyr Asp Tyr Ser Arg Lys Ser Asn
1               5                   10                  15

Leu Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 10
<211> LENGTH: 155
<212> TYPE: PRT
<213> ORGANISM: Homo sapiens
<220> FEATURE:
<223> OTHER INFORMATION: human IL-17A, including signal sequence

<400> SEQUENCE: 10

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 11
<211> LENGTH: 214
<212> TYPE: PRT
<213> ORGANISM: Artificial sequence
<220> FEATURE:
<223> OTHER INFORMATION: light chain anti-TNF antibody

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 12
<211> LENGTH: 451
<212> TYPE: PRT
<213> ORGANISM: Artificial sequence
<220> FEATURE:
<223> OTHER INFORMATION: heavy chain anti-TNF antibody

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 13
<211> LENGTH: 5
<212> TYPE: PRT
<213> ORGANISM: Artificial sequence
<220> FEATURE:
<223> OTHER INFORMATION: linker

<400> SEQUENCE: 13

Gly Gly Gly Gly Ser
1               5

<210> SEQ ID NO 14
<211> LENGTH: 10
<212> TYPE: PRT
<213> ORGANISM: Artificial sequence
<220> FEATURE:
<223> OTHER INFORMATION: linker

<400> SEQUENCE: 14

Gly Gly Gly Gly Ser Gly Gly Gly Gly Ser
1               5                   10

<210> SEQ ID NO 15
<211> LENGTH: 15
<212> TYPE: PRT
<213> ORGANISM: Artificial sequence
<220> FEATURE:
<223> OTHER INFORMATION: linker

<400> SEQUENCE: 15

```
Gly Gly Gly Gly Ser Gly Gly Gly Ser Gly Gly Gly Ser
1               5                   10              15
```

<210> SEQ ID NO 16
<211> LENGTH: 293
<212> TYPE: PRT
<213> ORGANISM: Artificial sequence
<220> FEATURE:
<223> OTHER INFORMATION: light chain anti-TNF antibody/linker/11L5-B06

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gly Val Thr Leu Phe Val Ala Leu Tyr Asp Tyr
225                 230                 235                 240

Ser Ala Arg Gly Gln Leu Asp Leu Ser Phe His Lys Gly Glu Lys Phe
                245                 250                 255

Gln Ile Leu Ser Thr His Glu Tyr Glu Asp Trp Trp Glu Ala Arg Ser
            260                 265                 270

Leu Thr Thr Gly Glu Thr Gly Tyr Ile Pro Ser Asn Tyr Val Ala Pro
        275                 280                 285

Val Asp Ser Ile Gln
    290
```

<210> SEQ ID NO 17
<211> LENGTH: 293
<212> TYPE: PRT
<213> ORGANISM: Artificial sequence
<220> FEATURE:
<223> OTHER INFORMATION: light chain anti-TNF antibody/linker/11L9-C09

<400> SEQUENCE: 17

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
    210                 215                 220

Gly Gly Gly Gly Ser Gly Val Thr Leu Phe Val Ala Leu Tyr Asp Tyr
225                 230                 235                 240

Glu Ser Val Ser Trp Ser Asp Leu Ser Phe His Lys Gly Glu Lys Phe
                245                 250                 255

Gln Ile Leu Ser Thr His Glu Tyr Glu Asp Trp Trp Glu Ala Arg Ser
                260                 265                 270

Leu Thr Thr Gly Glu Thr Gly Tyr Ile Pro Ser Asn Tyr Val Ala Pro
            275                 280                 285

Val Asp Ser Ile Gln
            290

<210> SEQ ID NO 18
<211> LENGTH: 7
<212> TYPE: PRT
<213> ORGANISM: Artificial sequence
<220> FEATURE:
<223> OTHER INFORMATION: Recombinant sequence

<400> SEQUENCE: 18

Ser Thr His Glu Tyr Glu Asp
 1               5

<210> SEQ ID NO 19
<211> LENGTH: 6
<212> TYPE: PRT
<213> ORGANISM: Artificial sequence
<220> FEATURE:
<223> OTHER INFORMATION: Recombinant RT-loop
```

```
<400> SEQUENCE: 19

Glu Ala Arg Thr Glu Asp
1               5

<210> SEQ ID NO 20
<211> LENGTH: 63
<212> TYPE: PRT
<213> ORGANISM: Homo sapiens

<400> SEQUENCE: 20

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
                20                  25                  30

Ser Glu Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60
```